US010783984B2

(12) United States Patent
Chin et al.

(10) Patent No.: US 10,783,984 B2
(45) Date of Patent: Sep. 22, 2020

(54) DE NOVO DIPLOID GENOME ASSEMBLY AND HAPLOTYPE SEQUENCE RECONSTRUCTION

(71) Applicant: Pacific Biosciences of California, Inc., Menlo Park, CA (US)

(72) Inventors: Chen-Shan Chin, San Leandro, CA (US); Paul Peluso, Meno Park, CA (US); David Rank, Menlo Park, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 586 days.

(21) Appl. No.: 15/162,315

(22) Filed: May 23, 2016

(65) Prior Publication Data

US 2016/0350478 A1 Dec. 1, 2016

Related U.S. Application Data

(60) Provisional application No. 62/166,605, filed on May 26, 2015.

(51) Int. Cl.
  *G16B 30/00* (2019.01)
  *G16B 20/00* (2019.01)
  *G16B 30/20* (2019.01)

(52) U.S. Cl.
  CPC ............. *G16B 30/00* (2019.02); *G16B 20/00* (2019.02); *G16B 30/20* (2019.02)

(58) Field of Classification Search
  None
  See application file for complete search history.

(56) References Cited

U.S. PATENT DOCUMENTS

| 6,917,726 | B2 | 7/2005  | Levene et al.    |
| 7,013,054 | B2 | 3/2006  | Levene et al.    |
| 7,056,661 | B2 | 6/2006  | Korlach et al.   |
| 7,170,050 | B2 | 1/2007  | Turner et al.    |
| 7,181,122 | B1 | 2/2007  | Levene et al.    |
| 7,292,742 | B2 | 11/2007 | Levene et al.    |
| 7,315,019 | B2 | 1/2008  | Turner et al.    |
| 7,476,503 | B2 | 1/2009  | Turner et al.    |
| 7,626,704 | B2 | 12/2009 | Lundquist et al. |
| 7,692,783 | B2 | 4/2010  | Lundquist et al. |
| 7,805,081 | B2 | 9/2010  | Lundquist et al. |
| 7,907,800 | B2 | 3/2011  | Foquet et al.    |
| 7,995,202 | B2 | 8/2011  | Lundquist et al. |
| 8,143,030 | B2 | 3/2012  | Maxham et al.    |
| 8,153,375 | B2 | 4/2012  | Travers et al.   |
| 8,182,993 | B2 | 5/2012  | Tomaney et al.   |
| 8,247,216 | B2 | 8/2012  | Zaccarin et al.  |
| 8,304,191 | B2 | 11/2012 | Eid et al.       |
| 8,335,029 | B2 | 12/2012 | Monadgemi        |
| 8,370,079 | B2 | 2/2013  | Sorenson et al.  |
| 8,465,922 | B2 | 6/2013  | Eid et al.       |
| 8,501,405 | B2 | 8/2013  | Korlach et al.   |
| 8,703,422 | B2 | 4/2014  | Tomaney et al.   |
| 9,175,338 | B2 | 11/2015 | Flusberg et al.  |
| 2009/0024331 | A1 | 1/2009  | Tomaney et al. |
| 2009/0298075 | A1 | 12/2009 | Travers et al. |
| 2010/0075309 | A1 | 3/2010  | Maxham et al.  |
| 2010/0075327 | A1 | 3/2010  | Maxham et al.  |
| 2010/0081143 | A1 | 4/2010  | Rank et al.    |
| 2010/0094041 | A1 | 4/2010  | Chen et al.    |
| 2010/0169026 | A1 | 7/2010  | Sorenson et al. |
| 2010/0311061 | A1 | 12/2010 | Korlach et al. |
| 2011/0117637 | A1 | 5/2011  | Gray et al.    |
| 2011/0183320 | A1 | 7/2011  | Flusberg et al. |
| 2011/0256631 | A1 | 10/2011 | Tomaney et al. |
| 2011/0257040 | A1 | 10/2011 | Turner et al.  |
| 2011/0257889 | A1 | 10/2011 | Klammer et al. |
| 2012/0015825 | A1 | 1/2012  | Zhong et al.   |
| 2012/0330566 | A1 | 12/2012 | Chaisson       |
| 2013/0138358 | A1 | 5/2013  | Tang et al.    |
| 2014/0025312 | A1 | 1/2014  | Chin et al.    |
| 2015/0178446 | A1 | 6/2015  | Tseng et al.   |

(Continued)

FOREIGN PATENT DOCUMENTS

WO   WO 2014/028771 A1   2/2014

OTHER PUBLICATIONS

Nagarajan et al. Sequence assembly demystified Nature Reviews Genetics vol. 14, pp. 157-167 (Year: 2013).*
Abello, et al., "*On Maximum Clique Problems in Very Large Graphs*", AT&T Labs Research Technical Report TR 98.32.1.
Cao et al. "*De Novo Assembly of a Haplotype-Resolved Human Genome*", Nature Biotechnology (Published online May 25, 2015) vol. 33, pp. 617-622, abstract, pg. 618, col. 1, para 3, col. 2 para 2-4, p. 619, col. 1 para 1-2, online methods, first page, col. 2, para 1, online methods, second page, col. 1, para 1-3, online methods, second page, col. 2 para 1, para 4, Fig. 1.
Eid, J., et al., "Real-Time DNA Sequencing from Single Polymerase Molecules", Science, vol. 323, p. 133, (2009).
Haszprunar, g., "*The Types of Homology and their Significance for Evolutionary Biology and Phylogenetics*", J. Evol. Biol., 5:13-24, 1992.

(Continued)

*Primary Examiner* — John S Brusca
(74) *Attorney, Agent, or Firm* — Morgan, Lewis & Bockius LLP

(57) ABSTRACT

Exemplary embodiments provide methods and systems for diploid genome assembly and haplotype sequence reconstruction. Aspects of the exemplary embodiment include generating a fused assembly graph from reads of both haplotypes, the fused assembly graph including identified primary contigs and associated contigs; generating haplotype-specific assembly graphs using phased reads and haplotype aware overlapping of the phased reads; merging the fused assembly graph and haplotype-specific assembly graphs to generate a merged assembly haplotype graph; removing cross-phasing edges from the merged assembly haplotype graph to generate a final haplotype-resolved assembly graph; and reconstructing haplotype-specific contigs from the final haplotype-resolved assembly graph resulting in haplotype-specific contigs.

23 Claims, 19 Drawing Sheets

(56) References Cited

U.S. PATENT DOCUMENTS

2015/0286775 A1    10/2015    Chin et al.

OTHER PUBLICATIONS

Henson et al. "*Next-Generation Sequencing and Large Genome Assemblies*", Pharmacogenomics. (Jun. 2012), vol. 13, No. 8, pp. 901-915. 901, col. 1, para 1, p. 902, col. 2 para 1, p. 906, col. 2., para 2-3, p. 907, col. 2 para 2, Fig. 2.

Huang et al. "*HaploMerger: Reconstructing Allelic Relationships for Polymorphic Diploid Genome Assemblies*", Genome Res. (Aug. 2012) vol. 22, No. 8, pp. 1581-1588, abstract , p. 1581, col. 2, para 3, p. 1582, col. 1, para 2-3, col. 2, para 2, p. 1583, col. 1, para 1, p. 1585, col. 1, para 2, col. 2, para 4, p. 1586, col. 1, para 2, para 3, para 4, para 6, col. 2 para 1, p. 1587, col. 2, para 1, Figs 1 and 2.

Iqbal et al. "*De Novo Assembly and Genotyping of Variants Using Colored de Bruijn Graphs*", Nature Genetics (Feb. 2012) vol. 44, No. 2, pp. 226-232, abstract, p. 227, col. 1, para 1, para 2, col. 2, para 3, Fig. 1 legend, Fig. 1.

Kececioglu, J.D., et al., "*Combinatorial Algorithms for DNA Sequence Assembly*", Algorithmica, vol. 13, p. 7-51 (1995).

Levene, et al., "*Zero-Mode Waveguides for Single-Molecule Analysis at High Concentrations*", Science vol. 299, p. 682 (2003).

Lind, et al., "*Next-Generation Sequencing: The Solution for High-Resolution, Unambiguous Human Leukocyte Antigen Typing*", Human Immunology, vol. 71, p. 1033-1042 (2010).

Myers, Eugene W., "*The Fragment Assembly String Graph*", Genes and Genomes, vol. 21, supl. 2, p. ii79-ii85, (2005).

Simpson et al. "*Efficient construction of an assembly string graph using the FM-index*", Bioinformatics.(Jun. 15, 2010) vol. 26, No. 12, pp. i367-i373, abstract, p. i370, col. 2, para 3, para 5, p. i371, col. 2, para 3.

Tseng, et al., "*Algorithms for Locating Extremely Conserved Elements in Multiple Sequence Alignments*", BMC Bioinformatics, 10:432 (2009).

Wang, et al., "*High-Throughput, High-Fidelity HLA Genotyping with Deep Sequencing*", Proc Natl Acad Sci, 109(22):8676-81 (2012).

Zagordi, et al., "*Error Correction of Next-Generation Sequencing Data and Reliable Estimation of HIV Quasispecies*", Nucleic Acids Research, vol. 38, n. 21, p. 7400-7409 (2010).

Töpfer, A. et al., "Viral Quasispecies Assembly via Maximal Clique Enumeration", PLOS Computational Biology, vol. 10, n. 2, Mar. 27, 2014.

Extended European Search Report, corresponding EP application No. 16800610.4.

\* cited by examiner

Add f:B, g:B, f:E, g:E as vertices
Add edges f:E→g:B and g:E→f:B

String Graph
800

Diploid Assembly

Remove Cross-Phasing Edges

Final Haplotype-Resolved Graph 207

Reconstruct Haplotigs

Haplotype 0 Contig

Haplotype 1 Contig

DE NOVO DIPLOID GENOME ASSEMBLY AND HAPLOTYPE SEQUENCE RECONSTRUCTION

CROSS-REFERENCE TO RELATED APPLICATIONS

This application claims the benefit of priority to U.S. Provisional Patent Application No. 62/166,605, filed May 26, 2015, and is related to U.S. patent application Ser. No. 14/574,887, filed Dec. 18, 2014, entitled "String Graph Assembly for Polyploid Genomes," assigned to the assignee of the present application, and incorporated herein by reference.

BACKGROUND OF THE INVENTION

Advances in biomolecule sequence determination, in particular with respect to nucleic acid and protein samples, have revolutionized the fields of cellular and molecular biology. Facilitated by the development of automated sequencing systems, it is now possible to sequence mixed populations of sample nucleic acids. However, the quality of the sequence information must be carefully monitored, and may be compromised by many factors related to the biomolecule itself or the sequencing system used, including the composition of the biomolecule (e.g., base composition of a nucleic acid molecule), experimental and systematic noise, variations in observed signal strength, and differences in reaction efficiencies. As such, processes must be implemented to analyze and improve the quality of the data from such sequencing technologies.

Besides affecting overall accuracy of sequence reads generated, these factors can complicate designation of a base-call as a true variant or, alternatively, a miscall (e.g., insertion, deletion, or mismatch error in the sequence read). For example, in a diploid organism a chromosome can have loci that differ in sequence from the homologous chromosome. When these loci are sequenced, the base calls will differ between the homologous chromosomes. It is important to be able to determine whether base calls that differ between homologous chromosomes are true variations between the homologues, or are merely sequencing errors. Yet further, a viral population in an individual can have many variations between individual viral genomes in the population, especially in highly mutable viruses such as HIV. Being able to identify different sequencing reads that have different origins (e.g., different chromosome or genome origins) is key to being able to accurately characterize a mixed population of nucleic acids. For a theoretical sequencing platform that generates reads that are 100% accurate, the reads can simply be compared to one another with simple string matching algorithms. Any difference between the reads is indicative of a true variant, and therefore, a different origin. However, any real-world raw sequencing data is likely to contain errors, so a simple string matching algorithmic approach will not be sufficient.

A string graph is a data structure that can be used to model a genome, e.g., to aid in assembling the genome from sequencing data. Modeling a genome with a string graph has generally advantages over modeling with an overlap graph or a de Brujin graph. For example, both correction of sequence and/or consensus errors and annotation of heterogeneous regions may be improved. For further details on string graph construction, see Fragment assembly string graph, Myers, E. W. (2005) Bioinformatics 21(iss. suppl. 2):ii79-ii85), of which is incorporated herein by reference.

Within a string graph, a vertex (also called a node) is a beginning and/or end of a sequence fragment, and an edge is the sequence fragment between two vertices. The core of the string graph algorithm is to convert each "proper overlap" (where only a portion of each of two reads overlaps the other read, i.e., the first read extends beyond the overlap at the 3' and the second read extends beyond the overlap at the 5' end) between two fragments into a string graph structure. This process comprises identifying vertices that are at the edges of an overlapping region and extending the edges to the non-overlapped parts of the overlapping fragments. The edge is labeled depending on the direction of the sequence and redundant edges are removed by transitive reduction to yield the string graph. For a double-stranded haploid sample, e.g., *E. coli* genome, this de-tangling will generate two complementary contigs, one for the forward strand and one for the reverse strand, which can be further reduced to a single contig that represents the genome assembly.

Additional features observed in string graph structures include branching, knots, and bubbles. Branching or branch points are typically caused when the reads contain some repetitive sequence, e.g. due to repeat regions in the genome. Knots, where many edges connect to the same node, can be caused by many reads that contain the same repeat in the genome. A simple "best overlapping logic" is typically used to "de-tangle" simple knots. Simple bubbles are generally observed where there are local structural variations, and are usually easy to resolve. However, simple bubbles can also be caused by errors in the original sequence reads and/or in the consensus determination performed during the pre-assembly of the reads. In addition, if the overlap identification step fails to detect a proper overlap, a bubble will be rendered in the string graph.

Complex bubbles may also be observed that may be generally caused by more complicated repeats within or between haplotypes. A conventional graph traversal algorithm will typically stop extending contigs around the nodes of such complex bubbles, but this often results in a fragmented assembly. One option is to use a greedy graph traversal algorithm, which may traverse the bubbles to generate larger contigs, but these are less likely to be truly representative of the original sample nucleic acid.

It is important to know how to detect and remove bubbles in the string graph caused by these artifacts, as well as how to differentiate the artificial bubbles from the bubbles caused by true structural variations between homologous sequences, and how to annotate those true variations. Accordingly, there is a need for improved de novo diploid assembly that incorporates both phasing between SNPs and structural variations for proper haplotype sequence reconstruction.

BRIEF SUMMARY OF THE INVENTION

The invention and various specific aspects and embodiments are better understood with reference to the following detailed descriptions and figures, in which the invention is described in terms of various specific aspects and embodiments. These are provided for purposes of clarity and should not be taken to limit the invention. The invention and aspects thereof may have applications to a variety of types of methods, devices, and systems not specifically disclosed herein.

In certain aspects, the invention provides methods for de novo diploid genome assembly and haplotype sequence reconstruction, the method performed by at least one software component executing on at least one processor. In certain embodiments, such methods comprise several steps including generating a fused assembly graph from reads of both haplotypes, the fused assembly graph including identified primary contigs and associated contigs; generating haplotype-specific assembly graphs using phased reads and haplotype aware overlapping of the phased reads; merging the fused assembly graph and haplotype-specific assembly graphs to generate a merged assembly haplotype graph; removing cross-phasing edges from the merged assembly haplotype graph to generate a final haplotype-resolved assembly graph; and reconstructing haplotype-specific haplotigs from the final haplotype-resolved assembly graph.

According to the methods disclosed herein, the exemplary embodiments provide algorithms that are capable of integrating multiple variant types into comprehensive assembled haplotypes.

DETAILED DESCRIPTION OF THE INVENTION

Various embodiments and components of the present invention employ signal and data analysis techniques that are familiar in a number of technical fields. For clarity of description, details of known analysis techniques are not provided herein. These techniques are discussed in a number of available reference works, such as: R. B. Ash. Real Analysis and Probability. Academic Press, New York, 1972; D. T. Bertsekas and J. N. Tsitsiklis. Introduction to Probability. 2002; K. L. Chung. Markov Chains with Stationary Transition Probabilities, 1967; W. B. Davenport and W. L Root. An Introduction to the Theory of Random Signals and Noise. McGraw-Hill, New York, 1958; S. M. Kay, Fundamentals of Statistical Processing, Vols. 1-2, (Hardcover—1998); Monsoon H. Hayes, Statistical Digital Signal Processing and Modeling, 1996; Introduction to Statistical Signal Processing by R. M. Gray and L. D. Davisson; Modern Spectral Estimation: Theory and Application/Book and Disk (Prentice-Hall Signal Processing Series) by Steven M. Kay (Hardcover—January 1988); Modern Spectral Estimation: Theory and Application by Steven M. Kay (Paperback—March 1999); Spectral Analysis and Filter Theory in Applied Geophysics by Burkhard Buttkus (Hardcover—May 11, 2000); Spectral Analysis for Physical Applications by Donald B. Percival and Andrew T. Walden (Paperback—Jun. 25, 1993); Astronomical Image and Data Analysis (Astronomy and Astrophysics Library) by J. L. Starck and F. Murtagh (Hardcover—Sep. 25, 2006); Spectral Techniques In Proteomics by Daniel S. Sem (Hardcover—Mar. 30, 2007); Exploration and Analysis of DNA Microarray and Protein Array Data (Wiley Series in Probability and Statistics) by Dhammika Amaratunga and Javier Cabrera (Hardcover—Oct. 21, 2003).

Computer Implementation

Figure 1:
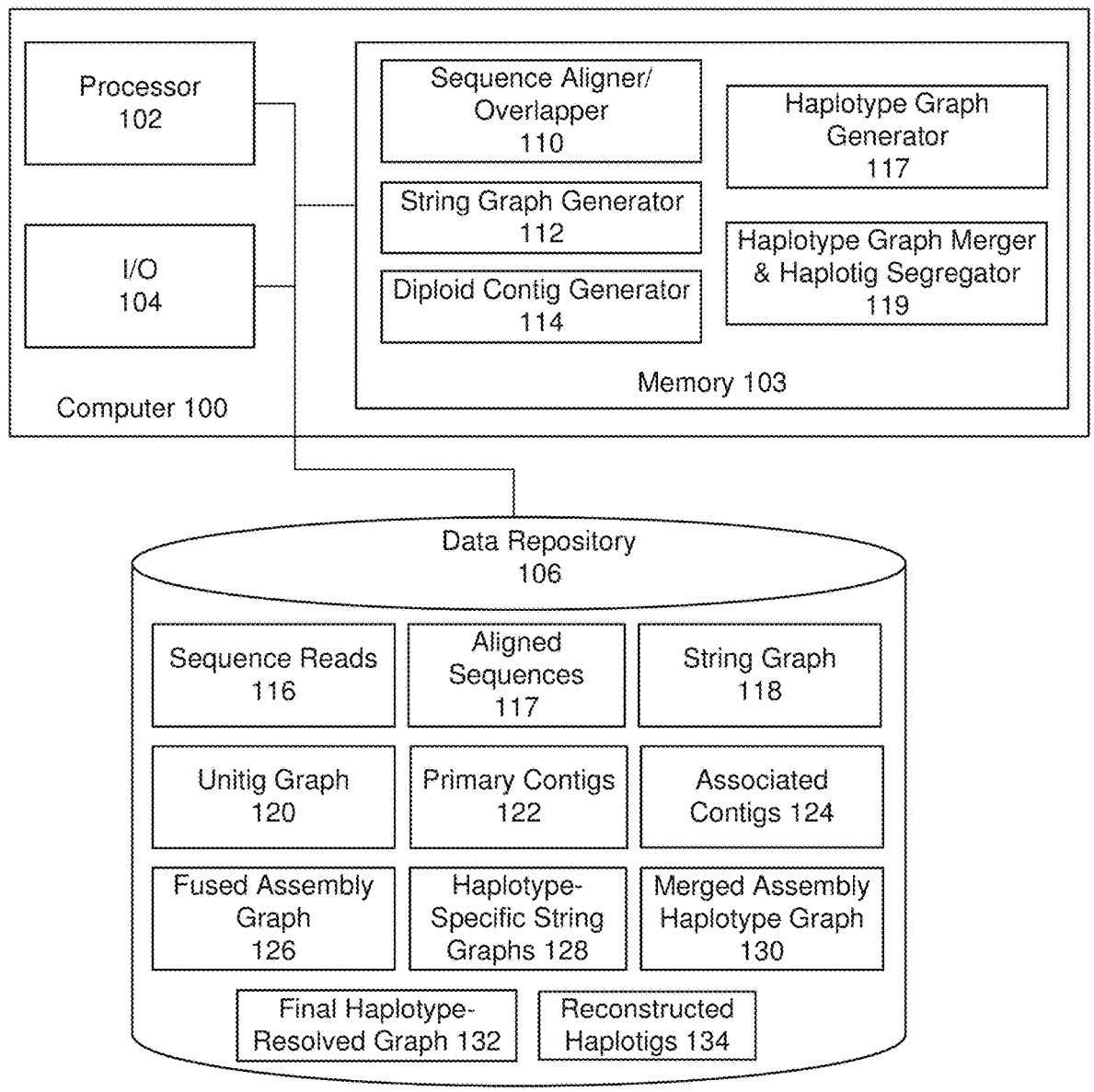
FIG. 1 is a diagram illustrating one embodiment of a computer system for implementing a process for de novo diploid genome assembly and haplotype sequence reconstruction.

FIG. 1 is a diagram illustrating one embodiment of a computer system for implementing a process for de novo diploid genome assembly and haplotype sequence reconstruction. In specific embodiments, the invention may be embodied in whole or in part as software recorded on fixed media. The computer 100 may be any electronic device having at least one processor 102 (e.g., CPU and the like), a memory 103, input/output (I/O) 104, and a data repository 106. The CPU 100, the memory 102, the I/O 104 and the data repository 106 may be connected via a system bus or buses, or alternatively using any type of communication connection. Although not shown, the computer 100 may also include a network interface for wired and/or wireless communication. In one embodiment, computer 100 may comprise a personal computer (e.g., desktop, laptop, tablet etc.), a server, a client computer, or wearable device. In another embodiment the computer 100 may comprise any type of information appliance for interacting with a remote data application, and could include such devices as an internet-enabled television, cell phone, and the like.

The processor 102 controls operation of the computer 100 and may read information (e.g., instructions and/or data) from the memory 103 and/or a data repository 106 and execute the instructions accordingly to implement the exemplary embodiments. The term processor 102 is intended to include one processor, multiple processors, or one or more processors with multiple cores.

The I/O 104 may include any type of input devices such as a keyboard, a mouse, a microphone, etc., and any type of output devices such as a monitor and a printer, for example. In an embodiment where the computer 100 comprises a server, the output devices may be coupled to a local client computer.

The memory 103 may comprise any type of static or dynamic memory, including flash memory, DRAM, SRAM, and the like. The memory 103 may store data and software components including a sequence aligner/overlapper 110, a string graph generator 112, a diploid contig generator 114, a haplotype graph generator 117 and a haplotype graph merger and haplotigs aggregator 119. These components are used in the process of sequence assembly as described herein, and are generally referred to collectively as the "assembler."

The data repository 106 may store several databases including one or more databases that store nucleic acid sequence reads (hereinafter, "sequence reads") 116, aligned sequences 117, a string graph 118, a unitig graph 120, primary contigs 122, associated contigs 124, a fused assembly graph 126, haplotype-specific string graphs 128, a merged assembly haplotype graph 130, a final haplotype-resolved assembly graph 132 and reconstructed haplotigs 134.

In one embodiment, the data repository 106 may reside within the computer 100. In another embodiment, the data repository 106 may be connected to the computer 100 via a network port or external drive. The data repository 106 may comprise a separate server or any type of memory storage device (e.g., a disk-type optical or magnetic media, solid state dynamic or static memory, and the like). The data repository 106 may optionally comprise multiple auxiliary memory devices, e.g., for separate storage of input sequences (e.g., sequence reads, reference sequences, etc.), sequence information, results of string graph generation (e.g., edges and nodes in a string graph, overlaps and branch points in assembly graphs), results of transitive reduction, and/or other information. Computer 100 can thereafter use that information to direct server or client logic, as understood in the art, to embody aspects of the invention.

In operation, an operator may interact with the computer 100 via a user interface presented on a display screen (not shown) to specify the sequence reads 116 and other parameters required by the various software programs. Once invoked, the software components in the memory 103 are executed by the processor 102 to implement the methods of the present invention.

The sequence aligner/overlapper 110 reads the selected sequence reads 116 from the data repository 106 and performs sequence alignment on the selected sequence reads 116 to identify regions of similarity that may be a consequence of structural or functional or other relationships between the sequence reads 116. Sequence reads 116 are generally high accuracy reads, e.g., at least about 98% or 99% accurate, and may be raw reads from a sequencing technology that provides such high quality reads, or may be pre-assembled, high-quality consensus reads constructed from sequencing read data of a lower quality, as described elsewhere herein. Aligned sequences 117 are generated by the sequence aligner/overlaper 110 during the sequence alignment. In certain embodiments, the sequence aligner/overlaper 110 is implemented in C, C++, Java, C #, F #, Python, Perl, Haskell, Scala, Lisp, a Python/C hybrid, and others known in the art.

The string graph generator 112 receives the resulting aligned sequences 117 and may generate the string graph 118 as well as the unitig graph 120 from the aligned sequences 117. The diploid contig generator 114 analyzes the string graph 118 and the unitig graph 120 and determines the primary contigs 122 and associated contigs 124, and generates a fused assembly graph 126 using reads from both haplotypes.

The haplotype graph generator 117 may generate haplotype-specific string graphs 128. The haplotype graph merger & haplotig segregator 119 reconstructs the haplotigs 134 by merging and processing the fused assembly graph 126 and the haplotype-specific string graphs 128 in accordance with exemplary embodiments, as explained further below.

During and after the above processes, results of this processing may be saved to the memory 103 and the data repository 106 and/or output through the I/O 104 for display on a display device and/or saved to an additional storage device (e.g., CD, DVD, Blu-ray, flash memory card, etc.), or printed. The result of the processing may include any combination of the primary contigs 122, the associated contigs 124, and the string graph 118, the fused assembly graph 126, the haplotype-specific string graphs 128, the merged assembly haplotype graph 130, the final haplotype-resolved assembly graph 132 and the haplotigs 134. The results may further comprise quality information, technology information (e.g., peak characteristics, expected error rates), alternate (e.g., second or third best) fused assembly graph 126, confidence metrics, and the like.

One of the main challenges in assembling diploid or polyploid genomes is that it is often difficult to distinguish between homologous sequences on different chromosomes, e.g., to identify individual haplotypes for the homologous chromosomes, or to analyze the size of a repetitive region, e.g., to determine the number of repeats in each homolog. Standard assembly algorithms assume the sequence reads all come from the same original nucleic acid molecule (e.g., chromosome). Conventional assembly algorithms often create a graph structure. As such, when analyzing a set of reads from multiple different, but similar nucleic acids (e.g., homologous chromosomes), the conventional assembly algorithms typically break resulting contigs at a junction where there is a fork in the assembly graph (e.g., unitig graph, overlap graph, string graph, De Bruijn graph, and the like) due to sequence differences between the homologs. These sequence differences create ambiguity on how to construct an assembly contig and result in the generation of many short contigs. See, e.g., Kececioglu, et al. (1995) Algorithmica 13 (1-2):7-51; and Myers, E. W. (2005) Bioinformatics 21(iss. suppl. 2):ii79-ii85), both of which are incorporated herein by reference in their entireties for all purposes.

This makes assembly of diploid or polyploid genomes into long contigs more difficult. In a diploid genome, the differences and the similarities between the two homologous copies can generate similar graph motifs to those caused by the repeats in a genome, and it can be difficult to distinguish between sequences from homologous templates, especially in repetitive regions. These complexities cause problems laying out the contigs when traversing the graph. An ideal layout method needs to be able to distinguish the different types of vertices in the graph and process them accordingly to generate the long contigs that can keep the genomic information together in a comprehensive and concise data structure/representation.

Accordingly, the exemplary embodiments are generally directed to powerful and flexible methods and systems for string graph assembly of polyploid genomes using long reads that generate long contigs comprising structural differences that distinguish between homologous sequences from multiple different nucleic acid molecules, repetitive sequences within a single nucleic acid molecule, and repetitive sequences within homologous sequences. The exemplary embodiments are further directed to a method of de novo assembly of diploid genomes in which both structural variations and phased SNPs are used to reconstruct haplotype sequences called haplotigs.

Figure 2:
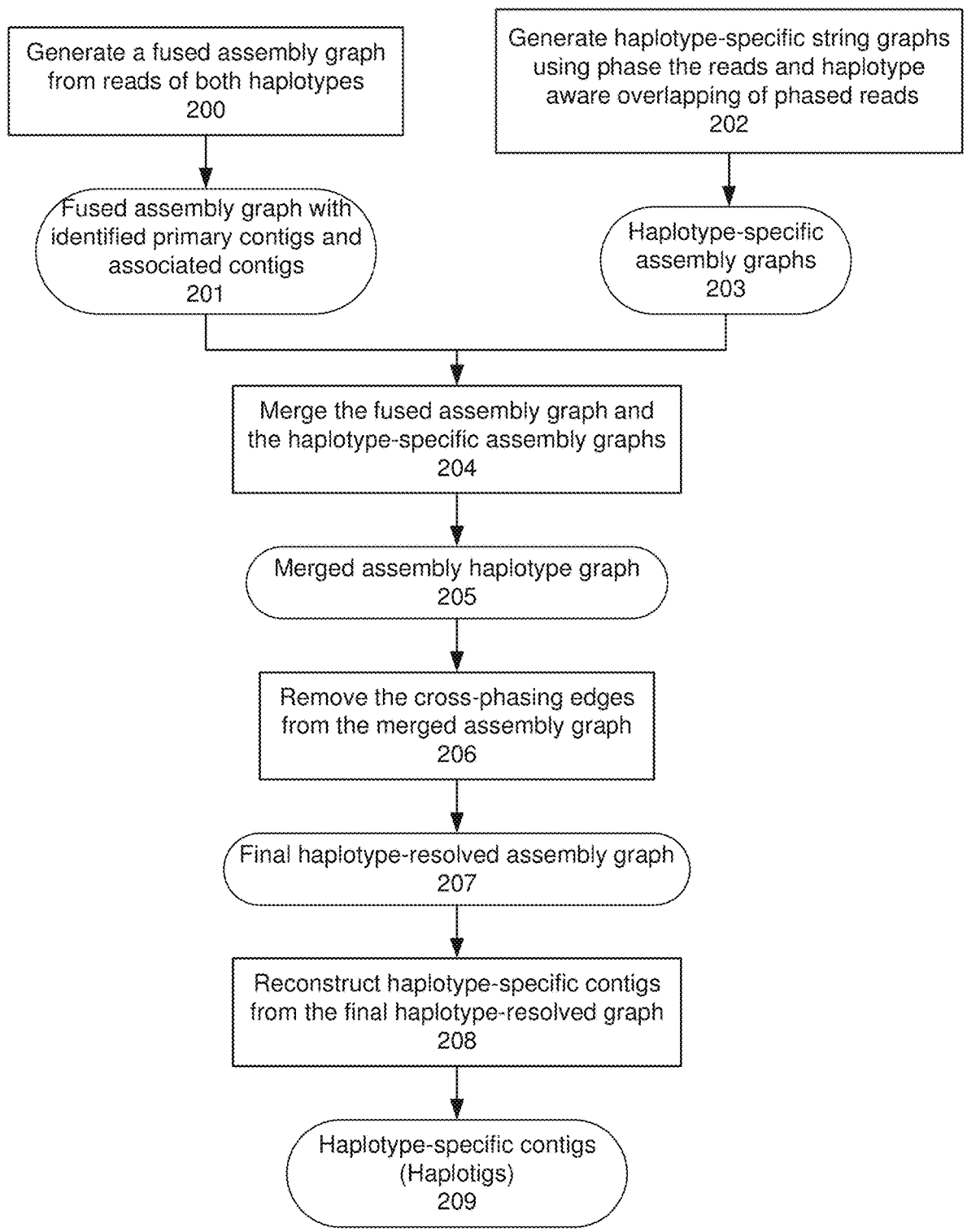
FIG. 2 is a flow diagram illustrating one exemplary embodiment process for de novo diploid genome assembly and haplotype sequence reconstruction.

FIG. 2 is a flow diagram illustrating one exemplary embodiment process for de novo diploid genome assembly and haplotype sequence reconstruction. In one embodiment, the method may be performed by one or more of the software components shown in FIG. 1 when executed by the processor 102. As will be apparent to one of skill in the art, the functionality of the software components in FIG. 1 may be configured into a lesser or greater number of modules/components.

The process may begin by generating a fused assembly graph from reads of both haplotypes (block 200), resulting in a fused assembly graph 201 having identified primary contigs and associated contigs. In one embodiment, the step of identifying the primary and associated contigs may be performed by the diploid contig generator 114.

The process also includes generating haplotype-specific assembly graphs using phased reads and haplotype aware overlapping of the phased reads (block 202), resulting in haplotype-specific assembly graphs 203. In one embodiment, the phased reads may comprise single-nucleotide polymorphisms (SNPs) aligned to a reference sequence, which optionally may comprise a primary contig of the fused assembly graph 201. Haplotype aware overlapping of the reads with the reference sequence results in construction of haplotype-specific assembly graphs 203. In one embodiment, this step may be performed by the haplotype graph generator 117.

The fused assembly graph 201 and haplotype-specific string graphs 203 are merged (block 204) to generate a merged assembly haplotype graph 205. Cross-phasing edges are removed from the merged assembly haplotype graph 205 to generate a final haplotype-resolved assembly graph 207 (block 206). Haplotype-specific contigs are then reconstructed from the final haplotype-resolved assembly graph 207 (block 208), resulting in haplotype-specific contigs (or haplotigs) 209. In one embodiment, the haplotype-specific contigs 209 include connected phasing blocks. In one embodiment, blocks 204, 206 and 208 may be performed by the haplotype graph merger & haplotig segregator 119. The above steps are described in further detail below.

Figure 3A:
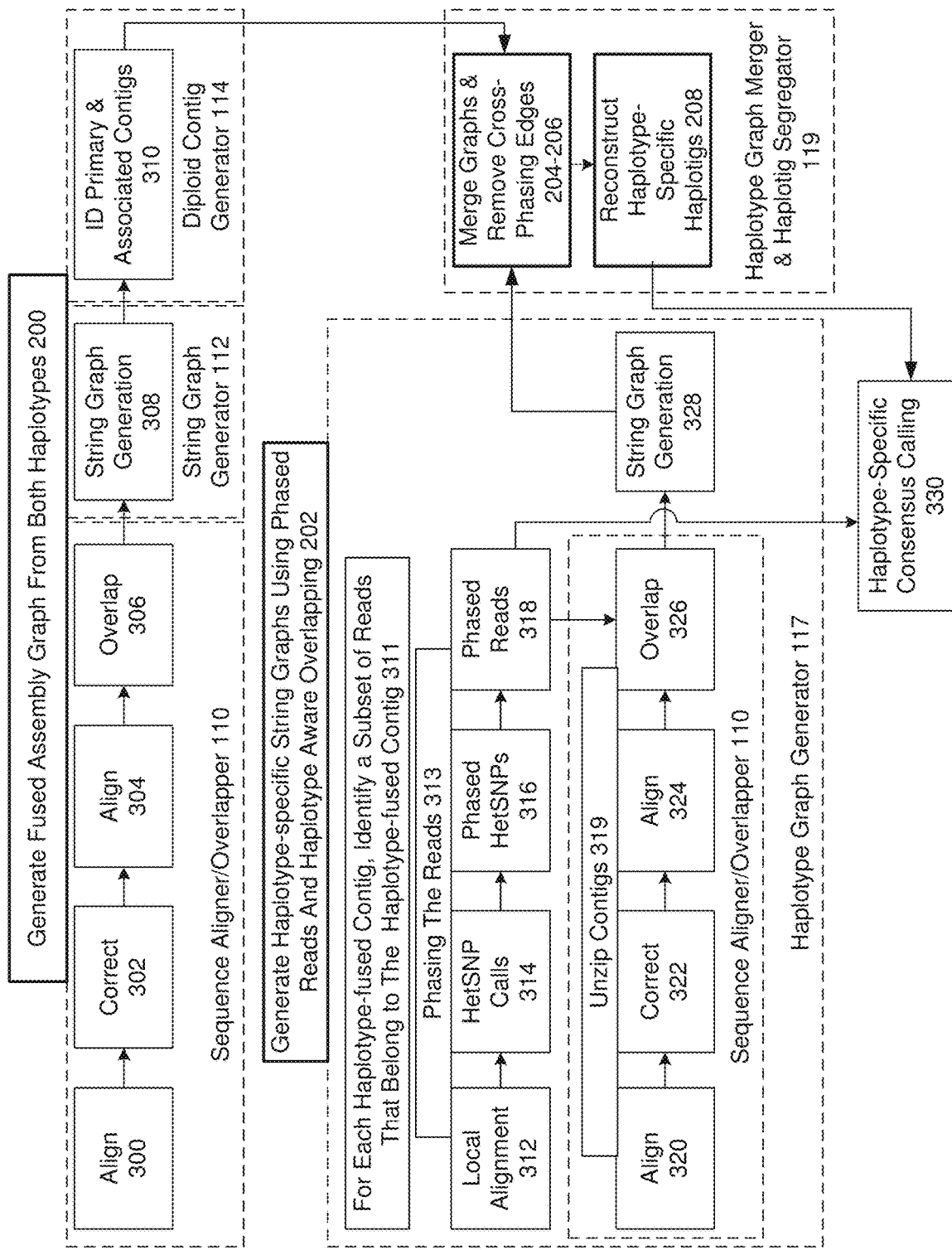
FIG. 3A is a block diagram illustrating the process blocks shown in FIG. 2 for reconstructing haplotype sequences in further detail.

FIG. 3A is a block diagram illustrating the process blocks shown in FIG. 2 for reconstructing haplotype sequences in further detail. Processing blocks 200, 202, 204-206 and 208 from FIG. 3A correspond to processing blocks 200, 202, 204-206 and 208 from FIG. 2. The dashed boxes illustrate which software components of FIG. 1 may be configured to perform the processing blocks shown according to one specific embodiment.

The process of generating a fused assembly graph from both haplotypes (block 200) includes an assembly process whereby the sequence aligner/overlapper 110 aligns (block 300) raw sequencing reads to identify regions of similarity between the sequences. The aligned sequences are then error corrected (block 302) to obtain a set of error-corrected reads, and the error-corrected reads are again aligned (block 304). Overlap filtering (block 306) finds overlapping read sequences and may discard reads that are contained within other overlapping reads. The string graph generator 112 generates a string graph from the overlapping reads.

The advantage of above method of the exemplary embodiments is that it effectively integrates multiple variant types into a single assembly.

The process of generating a fused assembly graph from both haplotypes is described in further detail immediately below and continues through a discussion of FIG. 13. This is followed by the details of the remaining steps of FIG. 3A starting with generating haplotype-specific string graphs (block 202).

Sequence Reads for Use in String Graph Construction

As described above with respect to FIG. 1, the string graph 118 may be generated by the string graph generator 112, which in turn, uses as input the aligned sequences 117 generated by the sequence aligner/overlaper 110 from the sequence reads 116. In another embodiment, rather than generating the string graph 118 locally, the string graph 118 may be generated on another computer or received from a third party for subsequent input to the diploid contig generator 114.

According to one aspect of the exemplary embodiment, the sequence reads 116 used as input to generate the string graph 118 are considered long sequencing reads, ranging in length from about 0.5 to 1, 2, 3, 5, 10, 15, 20, 60 or 100 kb. In preferred embodiments, these long sequencing reads are generated using a single polymerase enzyme polymerizing a nascent strand complementary to a single template molecule. For example, the long sequencing reads may be generated using Pacific Biosciences' single-molecule, real-time (SMRT®) sequencing technology. or by another long-read sequencing technology, such as nanopore sequencing The methods provided herein are useful for analyzing long sequence reads, which can traverse repetitive regions to provide unique sequence "anchors" at each end, i.e., outside of the repetitive region. The presence of two anchor sequences at opposite ends of or "flanking" a repetitive region allows the user to know the exact length of the repetitive region, and thereby distinguish the repetitive region on one homolog from the same region on another homolog, where the size of the region or one or both anchor sequences distinguishes between the two homologs. Yet further, long repeats are not always perfect, and often have sequence variants that interrupt the consensus repeat sequence. Having flanking sequence in a read comprising a repeat region allows the practitioner to accurately map these sequence variants within the repetitive region. This is difficult or impossible with short sequence reads, especially where the variants occur far from the flanking sequence.

In one embodiment, the sequence reads 116 may be generated using a single-molecule sequencing technology such that each read is derived from sequencing of a single template molecule. Single-molecule sequencing methods are known in the art, and preferred methods are provided in U.S. Pat. Nos. 7,315,019, 7,476,503, 7,056,661, 8,153,375, and 8,143,030; U.S. Ser. No. 12/635,618, filed Dec. 10, 2009; and U.S. Ser. No. 12/767,673, filed Apr. 26, 2010, all of which are incorporated herein by reference in their entirety for all purposes. In certain preferred embodiments, the technology used comprises a zero-mode waveguide (ZMW). The fabrication and application of ZMWs in biochemical analyses, and methods for calling bases in sequencing applications performed within ZMWs, e.g., sequencing-by-incorporation methods, are described, e.g., in U.S. Pat. Nos. 6,917,726, 7,013,054, 7,056,661, 7,170,050, 7,181,122, and 7,292,742, U.S. Patent Publication No. 20090024331, and U.S. Ser. No. 13/034,199 (filed Feb. 24, 2011), as well as in Eid, et al. (Science 323:133-138 (2009)) and Korlach, et al. (Methods Enzymol 472:431-455 (2010)) the full disclosures of which are incorporated herein by reference in their entirety for all purposes. In preferred embodiments, the sequence reads are provided in a FASTA file.

Sequence reads from various kinds of biomolecules may be analyzed by the methods presented herein, e.g., polynucleotides and polypeptides. The biomolecule may be naturally-occurring or synthetic, and may comprise chemically and/or naturally modified units, e.g., acetylated amino acids, methylated nucleotides, etc. Methods for detecting such modified units are provided, e.g., in U.S. Ser. No. 12/635,618, filed Dec. 10, 2009; and Ser. No. 12/945,767, filed Nov. 12, 2010, which are incorporated herein by reference in their entireties for all purposes. In certain embodiments, the biomolecule is a nucleic acid, such as DNA, RNA, cDNA, or derivatives thereof. In some preferred embodiments, the biomolecule is a genomic DNA molecule. The biomolecule may be derived from any living or once living organism, including but not limited to prokaryote, eukaryote, plant, animal, and virus, as well as synthetic and/or recombinant biomolecules. Further, each read may also comprise information in addition to sequence data (e.g., base-calls), such as estimations of per-position accuracy, features of underlying sequencing technology output (e.g., trace characteristics (integrated counts per peak, shape/height/width of peaks, distance to neighboring peaks, characteristics of neighboring peaks), signal-to-noise ratios, power-to-noise ratio, background metrics, signal strength, reaction kinetics, etc.), and the like.

In one embodiment, the sequence reads 116 may be generated using essentially any technology capable of generating sequence data from biomolecules, e.g., Maxam-Gilbert sequencing, chain-termination methods, PCR-based methods, hybridization-based methods, ligase-based methods, microscopy-based techniques, sequencing-by-synthesis (e.g., pyrosequencing, SMRT® sequencing, SOLiD™ sequencing (Life Technologies), semiconductor sequencing (Ion Torrent Systems), tSMS™ sequencing (Helicos BioSciences), Illumina® sequencing (Illumina, Inc.), nanopore-based methods (e.g., BASE™, MinION™, STRAND™), etc.). Sequence reads 116 may be generated by more than one sequencing technology. For example, some of the reads can be generated using a long-read sequencing technology as described above, while others of the reads can be generated using a short-read sequencing technology, e.g., having a higher accuracy. For example, such short reads can be generated using sequencers developed by Illumina or Life Technologies. Combining long reads having a lower accuracy with short reads having a higher accuracy can provide a final assembly that is both very long and very accurate. However, given a high enough fold-coverage of long reads, extremely high accuracy can also be achieved using only long reads. In contrast, using only short reads at high coverage is unlikely to significantly increase the length of contigs in the final assembly and generally results in a highly fragmented assembly.

In certain embodiments, the sequence information analyzed may comprise replicate sequence information. For example, replicate sequence reads may be generated by repeatedly sequencing the same molecules, sequencing templates comprising multiple copies of a target sequence, sequencing multiple individual biomolecules all of which contain the sequence of interest or "target" sequence, or a combination of such approaches. Replicate sequence reads need not begin and end at the same position in a biomolecule sequence, as long as they contain at least a portion of the target sequence. For example, in certain sequence-by-synthesis applications, a circular template can be used to generate replicate sequence reads of a target sequence by allowing a polymerase to synthesize a linear concatemer by continuously generating a nascent strand from multiple passes around the template molecule. Replicate sequences generated from a single template molecule are particularly useful for determining a consensus sequence for that template molecule. This "single-molecule consensus" determination is distinct from the conventional methods for determining consensus sequences from reads of multiple template molecules, and is particularly useful for identifying rare variants that might otherwise be missed in a large pool of sequence reads from multiple templates. Examples of methods of generating replicate sequence information from a single molecule are provided, e.g., in U.S. Pat. No. 7,476,503; U.S. Patent Publication No. 20090298075; U.S. Patent Publication No. 20100075309; U.S. Patent Publication No. 20100075327; U.S. Patent Publication No. 20100081143, U.S. Ser. No. 61/094,837, filed Sep. 5, 2008; and U.S. Ser. No. 61/099,696, filed Sep. 24, 2008, all of which are assigned to the assignee of the instant application and incorporated herein by reference in their entireties for all purposes.

In some embodiments, the accuracy of the sequence read data initially generated by a sequencing technology discussed above may be approximately 70%, 75%, 80%, 85%, 90%, or 95%. Since efficient string graph construction preferably uses high-accuracy sequence reads, e.g., preferably at least 98% accurate, where the sequence read data generated by a sequencing technology has a lower accuracy, the sequence read data may be subjected to further analysis, e.g., overlap detection, error correction etc., to provide the sequence reads 116 for use in the string graph generator 112. For example, the sequence read data can be subjected to a pre-assembly step to generate high-accuracy pre-assembled reads, as further described elsewhere herein.

For ease of discussion, various aspects of the invention will be described with regards to analysis of polynucleotide sequences, but it is understood that the methods and systems provided herein are not limited to use with polynucleotide sequence data and may be used with other types of sequence data, e.g., from polypeptide sequencing reactions.

Generating Pre-Assembled Reads

In certain embodiments, sequence read data is used to create "pre-assembled reads" having sufficient quality/accuracy for use as sequence reads 116 in the string graph generator 112 to construct the string graph 118. A pre-assembly sequence aligner (which may also be referred to as an aggregator) may perform pre-assembly of the sequence read data generated from a sequencing technology (e.g., SMRT® Sequencing or nanopore-based sequencing) to provide the sequence reads 116. Preferably, the pre-assembly sequence aligner is very efficient, and certain preferred aligners/aggregators and embodiments for generating pre-assembled reads are described in detail in U.S. patent application Ser. No. 13/941,442, filed Jul. 12, 2013; 61/784,219, filed Mar. 14, 2013; and 61/671,554, filed Jul. 13, 2012, which are incorporated herein by reference in their entireties for all purposes.

The alignment and consensus algorithm used during pre-assembly is preferably fast, e.g., using simple sorting and counting. In some embodiments, the alignment operation comprises choosing a best-match sequence read from the nucleic acid sequence read data as a seed sequence, followed by aligning remaining reads in the sequence read data to the seed sequence to generate the set of pre-assembly aligned sequences.

In specific embodiments, a set of sequence reads for a region of interest or "target" region (optionally from a mixed population) is generated or otherwise provided, and these sequence reads (e.g., preferably in a FASTA file) are aligned to one another to form a set of sequence alignments. In specific embodiments, a set of "seed" sequence reads is selected and these seed reads are typically selected from the longest sequence reads in the set, e.g., reads that are at least 3, 4, 5, 6, 8, 10 or 20 kb in length. All the sequence reads in the set are aligned against each of the seed reads, to generate a set of alignments between the reads and the seed reads and, thereby, map each of the reads in the set to at least one seed read. An alignment-and-consensus process is used to construct single "pre-assembled long reads" for each of the seed reads using all of the reads that map to that seed read. First, the set of sequence alignments generated with the seed read is normalized and used to construct a sequence alignment graph (SAG) analogous to multiple sequence alignment. Then, a consensus sequence for the set of sequence reads mapping to that seed read is derived from the SAG, and this consensus sequence can be thought of as representing the "average" sequence of the reads from the mixed population that map to that seed read. Where different seed reads map to each other, those seed reads and all the sequences that map thereto can be combined in a single alignment to derive a single consensus sequence for a resulting pre-assembled long read. In preferred embodiments, pre-assembly is executed using an algorithm based on encoding multiple sequence alignments with a directed acyclic graph to find the best path for the best consensus sequence, and this method is an effective strategy for removing random insertion and missing errors that were present in the original sequence reads.

Optionally, such as when homologous sequences are to be resolved during the pre-assembly step and prior to the string graph analysis, the sequence reads in the sequence alignment graph are partitioned or "clustered" based upon the structure of the graph to generate a plurality of subsets of the set of sequence reads. For each subset, the constituent sequence reads are aligned and used to construct a sequence alignment graph, which is used to generate a consensus sequence. Optionally, the new consensus sequences are compared (e.g., by alignment and standard statistical analysis) to reference sequences to identify the source of the sequence reads of the subset of sequence reads from which the consensus sequence was derived. For example, a consensus sequence for a subset may be compared to multiple different reference haplotype sequences for a genomic region of interest, and the reference sequence that best matches the subset consensus sequence is indicative of the haplotype of the original template nucleic acid that was sequenced to generate the sequence reads in the subset. This embodiment is particularly useful for resolving SNP-level diploid sequence variants during the pre-assembly step.

Following the pre-assembly of the sequence reads and determination of the pre-assembly consensus sequence(s), the accuracy of the consensus sequence is typically at least 99%, and often at least 99.5%. As such, these highly-accurate consensus sequences are suitable to serve as an input (e.g., sequence reads 116) to the string graph assembly method described here.

Generating the String Graph

Once the sequence reads 116 are provided, they are subjected to alignment and overlap detection by the sequence aligner/overlapper 110, which generates aligned sequences 117. Preferably, the sequence aligner/overlapper 110 is very efficient and fast, e.g., using simple sorting and counting, and certain preferred aligners/aggregators are known in the art and/or described with respect to the pre-assembly step, above. The string graph generator 112 generates the string graph 118 from the aligned sequences 117 by a series of steps described further below.

Figure 3B:
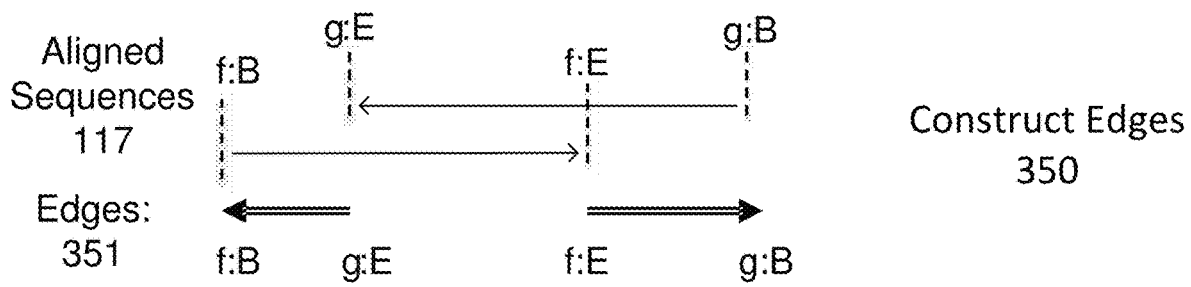
FIGS. 3B and 3C are diagrams illustrating embodiments of methods for creating a string graph from overlaps between aligned sequences and transitive reduction.
Figure 3C:
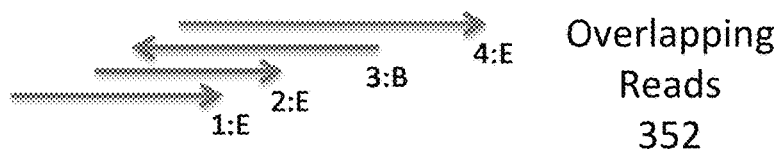
Figure 3C:
Figure 3C:
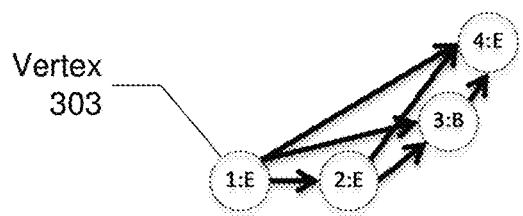
Figure 3C:
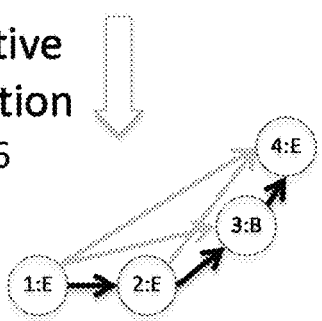

FIGS. 3B and 3C are diagrams illustrating embodiments of methods for creating a string graph from overlaps between aligned sequences and transitive reduction. As an overview, the string graph generator 112 may generate the string graph 118 by constructing edges 350 from the aligned, overlapping sequences 117 based on where the reads overlap one another. The core of the string graph algorithm is to convert each "proper overlap" between two aligned sequences into a string graph structure. In FIG. 3B, two overlapping reads (aligned sequences 117) are provided to illustrate the concepts of vertices and edges with respect to overlapping reads. Specifically, the vertices right at the boundaries of an overlap are g:E and f:E are identified as the "in-vertices" of the new edges to be constructed. Edges 351 are generated by extending from the in-vertices to the ends of the non-overlapping parts of the aligned reads, which are identified as the "out-vertices," e.g., f:E to g:B (out-vertex) and g:E to f:B (out-vertex). If the sequence direction is the same as the direction of the edges, the edge is labeled with the sequence as it is in the sequence read. If the sequence direction is opposite that of the direction of the edges, the edge is labeled with the reverse complement of the sequences.

In FIG. 3C, the four aligned, overlapping reads 352 are used to create an initial graph 354, and the initial graph 354 is subjected to transitive reduction 356 and graph reduction, e.g., by "best overlapping," to generate the string graph 118. Detecting overlaps in the aligned sequences 117 (also referred to as overlapping reads) may be performed using overlap-detection code that functions quickly, e.g., using k-mer-based matching.

Converting the overlapping reads 352 into the initial graph 354 may comprise identifying vertices that are at the edges of an overlapping region and extending them to the ends of the non-overlapped parts of the overlapping fragments. Each of the edges (shown as the arrows in initial graph 354) is labeled depending on the direction of the sequence. Thereafter, redundant edges are removed by transitive reduction 356 to yield the string graph 118. Further details on string graph construction are provided in Myers, E. W. (2005) Bioinformatics 21, suppl. 2, pgs. ii79-ii85, which is incorporated herein by reference in its entirety for all purposes.

Figure 4:
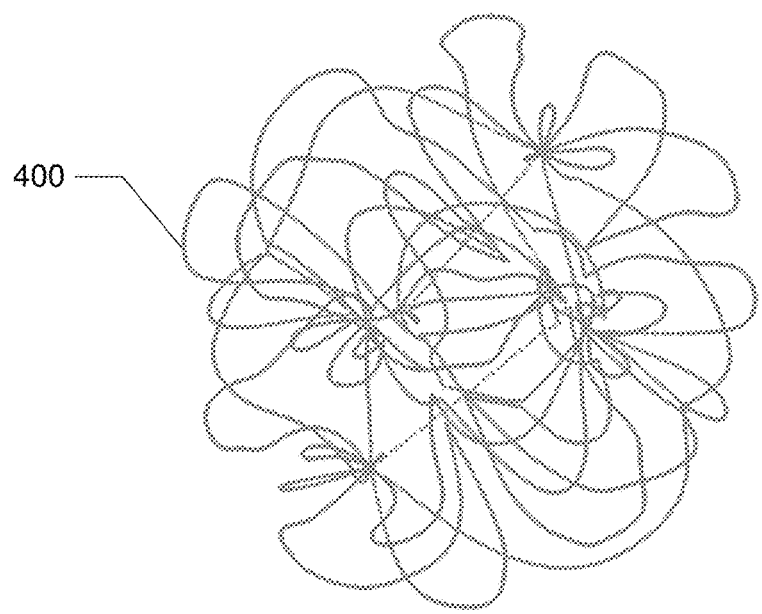
FIG. 4 is a diagram graph illustrating an exemplary string graph generated for a double-stranded haploid sample, e.g., *E. coli* genome.

FIG. 4 is a diagram graph illustrating an exemplary string graph 400 generated for a double-stranded haploid sample, e.g., *E. coli* genome, using 10× 10,000 base pair (bp) reads, resulting in a string graph comprising 9278 nodes and 9536 edges.

Figure 5:
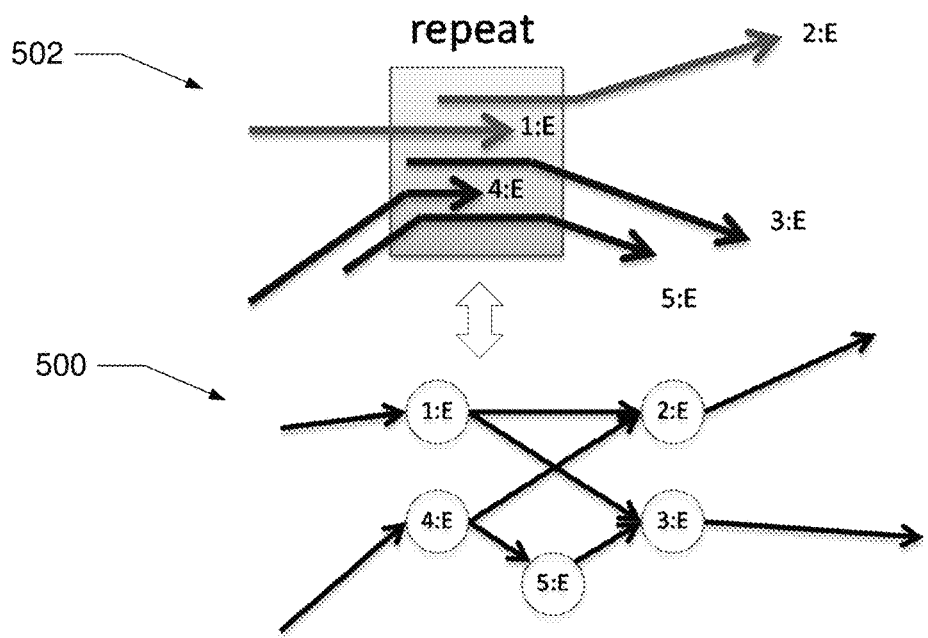
FIG. 5 is a diagram showing that additional features observed in string graph structures may include areas of entanglement such as branching, knots, and bubbles.

FIG. 5 is a diagram showing that additional features observed in string graph structures 500 may include areas of entanglement such as branching, knots, and bubbles. Branching or branch points are typically caused by the presence of repeated sequences 502 in the aligned sequences 117, but can also be due to the presence of homologous sequences, e.g., where the sample is diploid, and chimeras in the sequence read data can also mimic a repeat region creating an unnecessary branch in the graph. Knots can be caused when an overlap region falls fully within a repetitive region. A simple "best overlapping rule" is typically used to "de-tangle" the knots.

Figure 6:
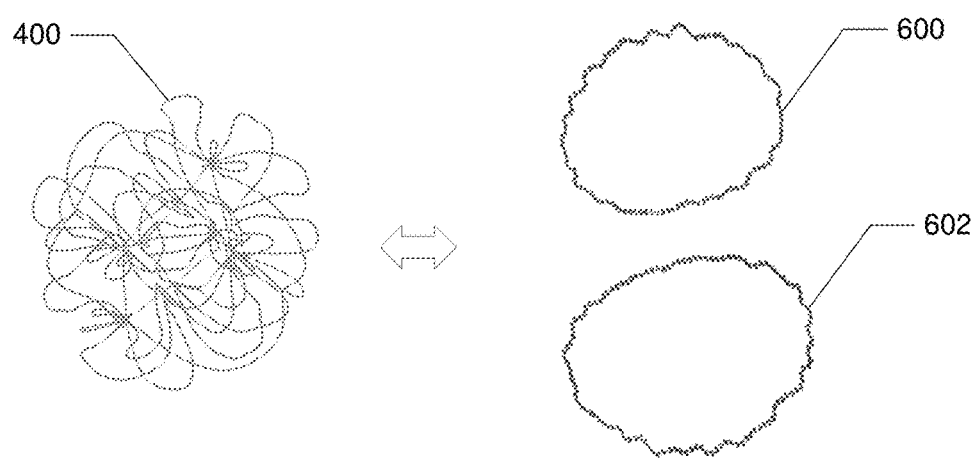
FIG. 6 is a diagram showing results of applying the best overlapping rule on the *E. coli* string graph.

FIG. 6 is a diagram showing results of applying the best overlapping rule on the *E. coli* string graph 400. As shown, after the best overlapping rule is applied to the string graph with 400, this "de-tangling" will generate two complementary contigs, one forward strand 600 and one reverse strand 602.

Generate a Unitig Graph

Once the string graph has been generated, the unitigs are identified in the string graph and generates a unitig graph. In one embodiment, non-branching unitigs within the string graph are identified to form the unitig graph, where unitigs represent the contigs that can be constructed unambiguously from the string graph and that correspond to the linear paths in the string graph without any branch induced by repeats or sequencing errors.

Figure 7:
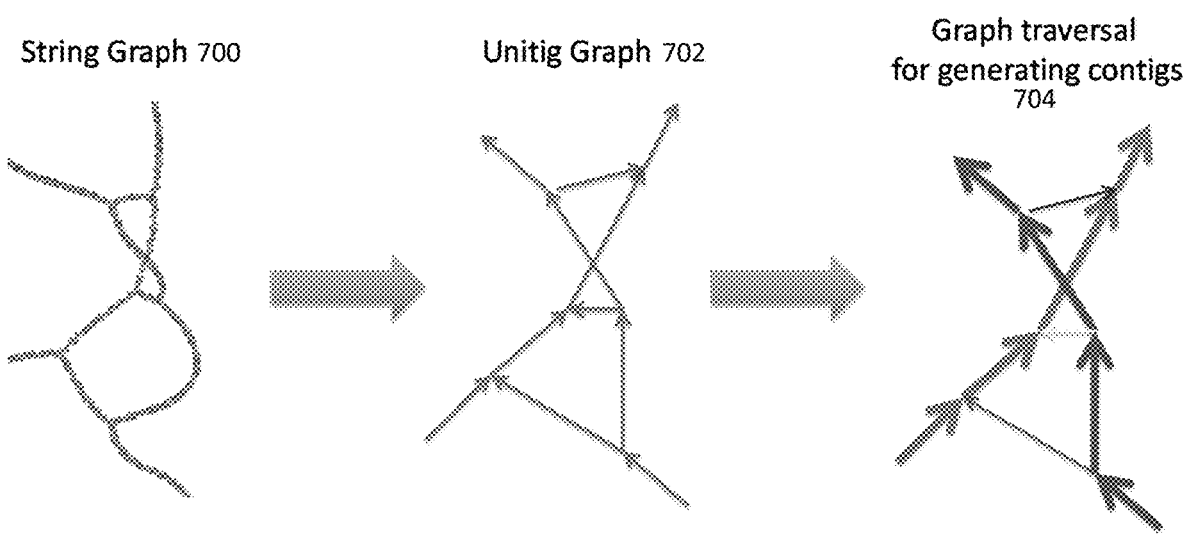
FIG. 7 is a diagram graphically illustrating identifying unitigs from the non-branching parts of the string graph to generate a unitig graph.

FIG. 7 is a diagram graphically illustrating identifying unitigs from the non-branching parts of the string graph 700 to generate a unitig graph 702, which simplifies the initial string graph into the unitig graph with simple paths in which all the edges and a path without any branching nodes are formed into a single edge. Graph traversal is performed on the unitig graph 702 to generate the contigs 704, which are a contiguous set of overlapping sequences, as shown. Flexible graph construction and graph traversal methods are preferred, e.g., and may be implemented in Python or other computer language, as listed elsewhere herein.

Problems with Conventional String Graph Assembly

Figure 8A:
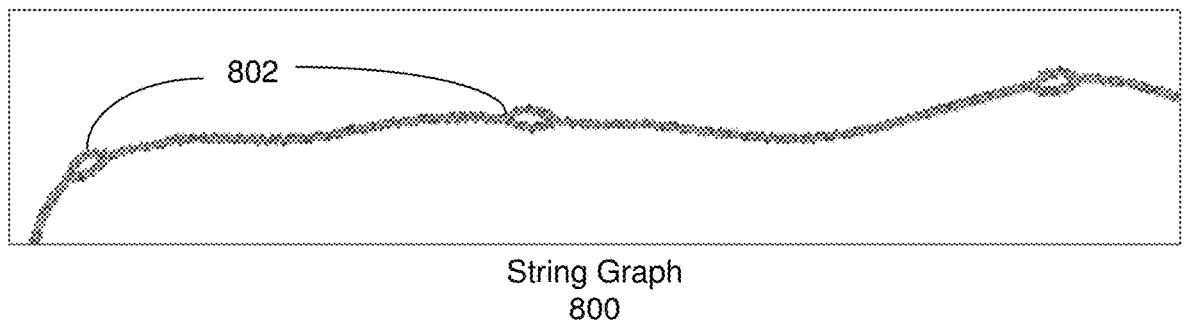
FIG. 8A is a diagram graphically illustrating that a string graph that may have a quasi linear structure and bubbles.
Figure 8B:
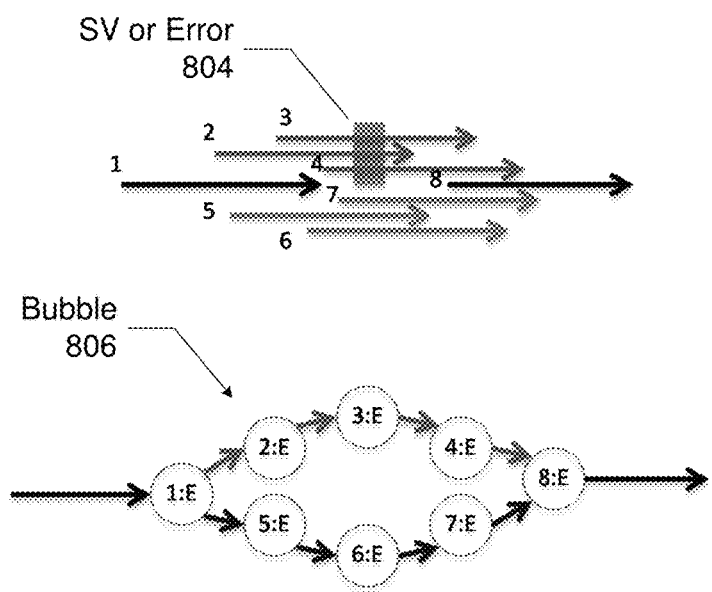
FIG. 8B is a diagram illustrating that simple bubbles can also be caused by errors in the original sequence reads and/or in the consensus determination performed during the pre-assembly of the reads.

FIG. 8A is a diagram graphically illustrating a string graph 800 having a quasi linear structure and bubbles 802. Simple bubbles 802 may be generally observed in a string graph 800 where there are local structural variations (SV) between haplotypes. As shown in FIG. 8B, simple bubbles 802 can also be caused by errors in the original sequence reads and/or in the consensus determination performed during the pre-assembly of the reads. If the overlap identification step fails to detect a proper overlap 804 between the reads (e.g., due to a structural variation or sequencing error), a bubble 806 will be rendered in the string graph.

It is important to know how to detect and resolve bubbles caused by these artifacts, as well as how to differentiate the artifactual bubbles, e.g., caused due to sequencing errors, from the bubbles caused by true structural variations between homologous sequences, and how to annotate those true variations. Simple bubbles are usually easy to resolve, but complex bubbles are more difficult to resolve. Complex bubbles are generally caused by more complicated repeats or other larger-scale structural variations within or between haplotypes.

Figure 9:
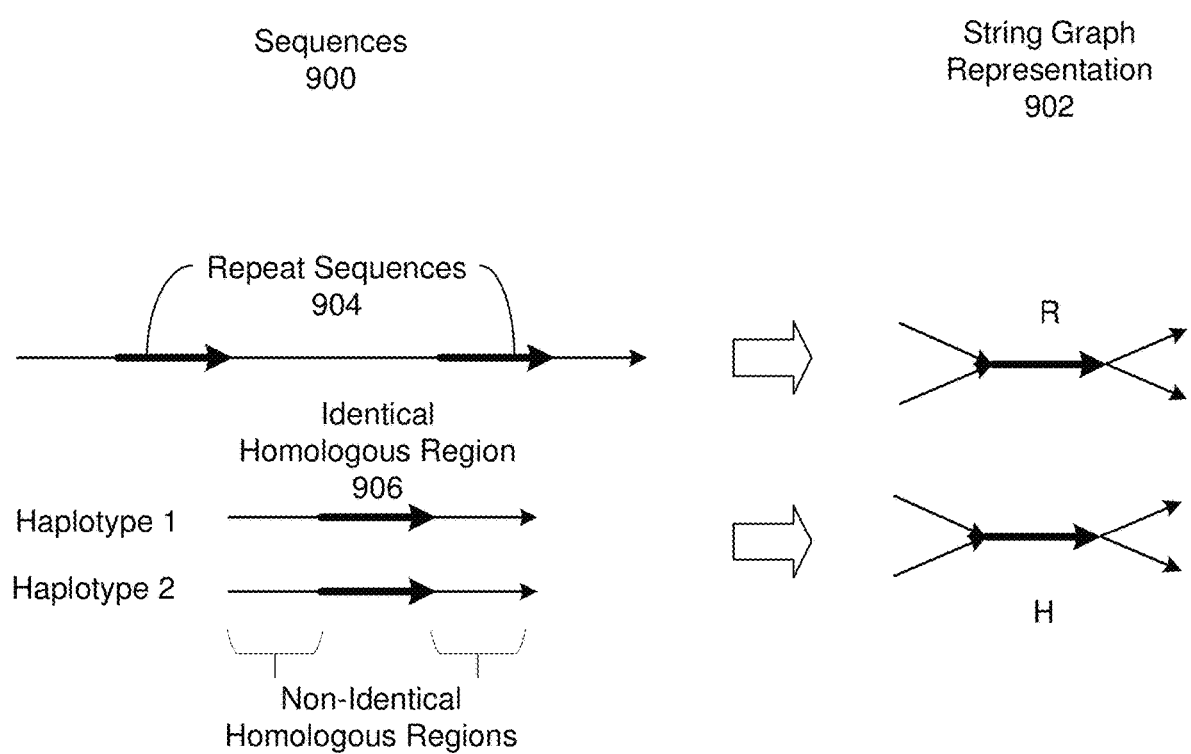
FIG. 9 is a diagram illustrating one challenge of diploid assembly is to determine the genetic sequence underlying complex structures in a string graph where the same structure in the string graph can be caused by repeats or the presence of homologous sequences.

FIG. 9 is a diagram illustrating one challenge of diploid assembly is to distinguish between similar topologies in a string graph caused by two different types of underlying nucleotide sequence structures in a genome. Sequences 900 having different types of nucleotide sequence structures may have string graph representations 902 that have the same local topology and are therefore difficult to distinguish by conventional assemblers, which focus on local topology rather than regional topology extending over a larger portion of the graph. The string graph representations 902 are illustrating that the region indicated by the dark arrow is present multiple times in the sequences used to generate the graph, and that the sequences on either side of it are different (e.g., due to sequence variants, mutations, different locations on a chromosome, etc.).

This string graph representation does not distinguish between whether the underlying nucleotide sequence comprises identical sequences at different positions on a single nucleic acid strand (e.g., on a single chromosome strand or fragment thereof), as shown for repeats sequences 904 (also referred to as repeats, R), or comprises identical sequences on different nucleic acid strands, e.g., homologous chromosomes, as shown for identical homologous sequences 906. For example, haplotype 1 and haplotype 2 may be from different homologous chromosomes, e.g., one maternal chromosome and one paternal chromosome, and the dark arrow is indicative of a region of the chromosomes that is identical between the two homologs. In both cases, the string graph assembly combines the matching regions (e.g., repeats (R) or identical homologous regions (H)) into a single segment in the graph. Therefore, the resulting string graph representation 902 has the same topology regardless of the underlying sequence structure. The determination of the true, underlying sequence structure can be even more difficult to resolve where there is repeating sequence within homologous regions (not shown).

The string graph representations 902 of both repeat sequences 904 and identical homologous sequences 906 basically have the same the local structure, as shown, which may be one underlying cause of complex bubbles in the string graph. During assembly, it is desirable to distinguish between these two types of nucleotide sequence structures in order to construct a sequence assembly that accurately represents the sequences of the original sample nucleic acid from which the sequence read data was generated.

Figure 10A:
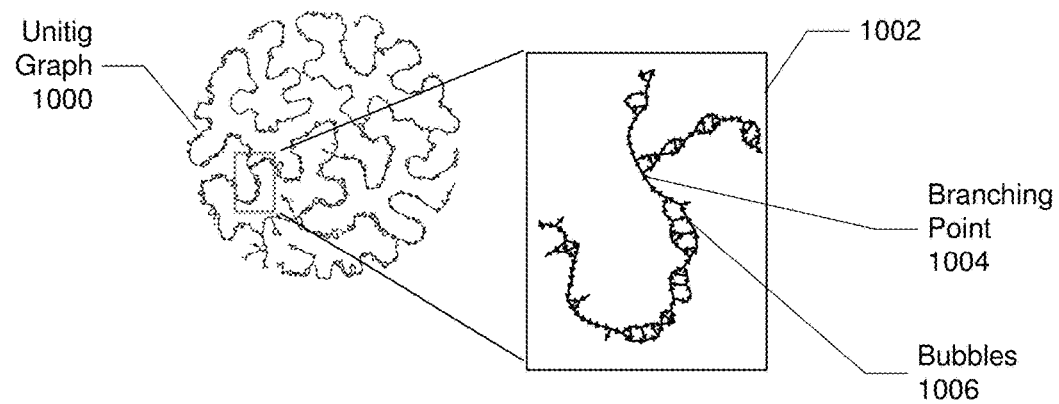
FIGS. 10A and 10B are diagrams graphically illustrating exemplary large- and small-scale topological features of a unitig graph.
Figure 10B:
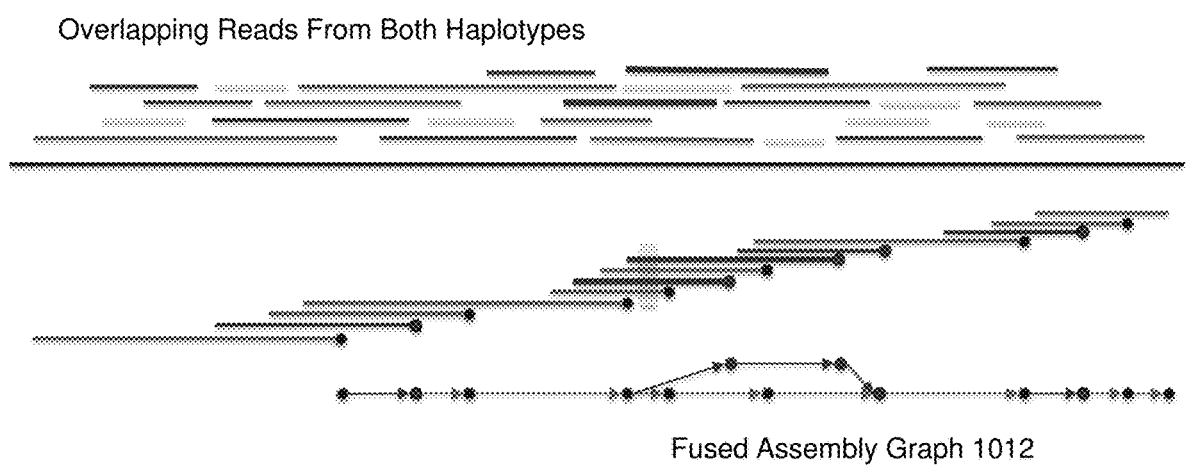

FIGS. 10A and 10B are diagrams graphically illustrating exemplary large and small scale topological features of the unitig graph 1000. The graph in FIG. 10A was generated from genomic sequence data from *Arabidopsis thaliana*, as described in the EXAMPLE. An enlarged portion 1002 of the string graph 1000 shows both bubbles 1006 caused by structural variations between the homologous copies, as well as a branching point 1004 caused by the presence of repeats in the sequence reads.

As shown in FIG. 10B, one problem presented by such topological features in the string graph 1000 is that conventional graph traversal algorithms typically stop extending contigs around the nodes of such complex bubbles in the graph and only identify non-branching simple paths because the conventional methods do not analyze the large scale string graph structure. Continuity may be improved by performing a fused string graph assembly that utilizes the longest paths from both haplotypes to create a fused assembly graph 1012.

Referring again to FIG. 2, the diploid contig generator 114 addresses the issues caused by large scale structural variations by identifying primary and associated contigs 310 from the string graph. In contrast to conventional graph traversal algorithms, the diploid contig generator 114 of the exemplary embodiments is capable of distinguishing between different large-scale topologies in a string graph, e.g., complex bubbles caused by repeats or homologous regions, or true branch points, without requiring the use of additional reads.

Figure 11A:
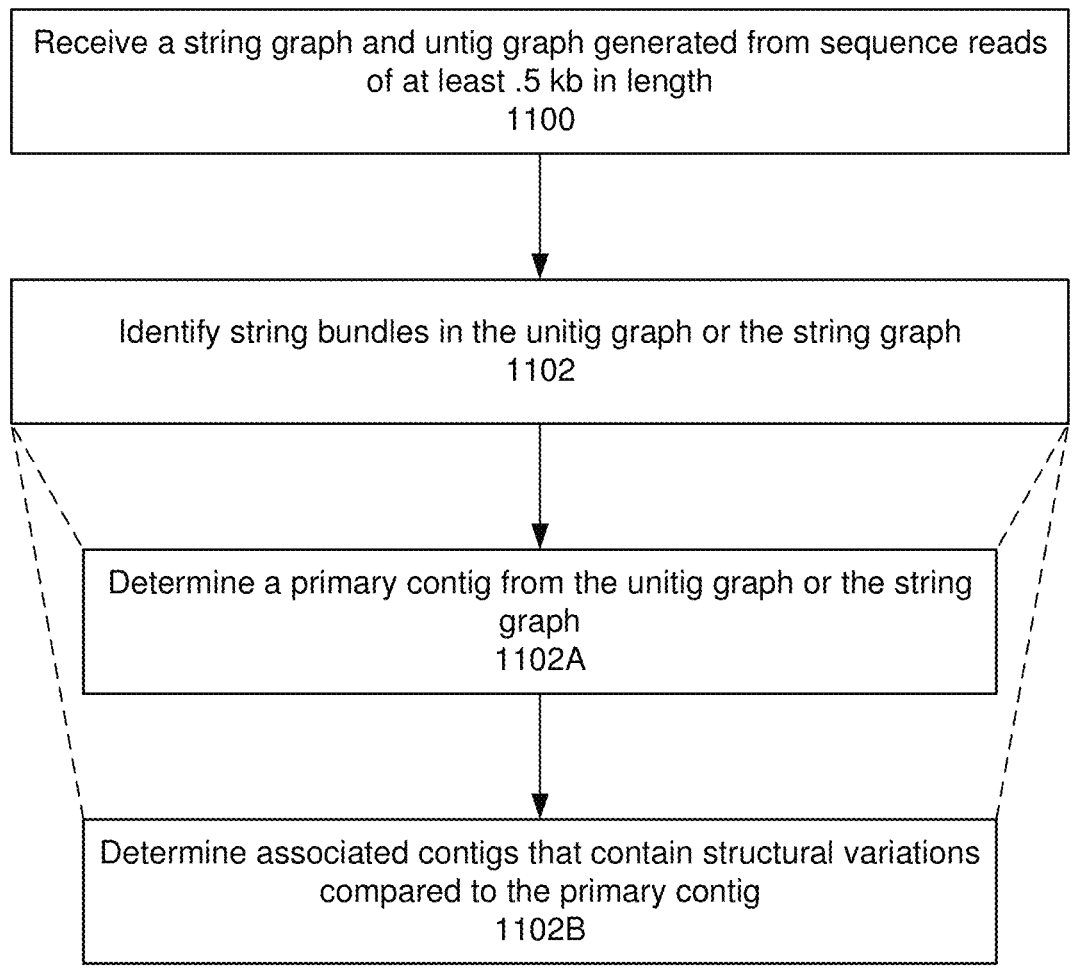
FIG. 11A is a flow diagram illustrating the process for string graph assembly of polyploid genomes performed by the diploid contig generator.

FIG. 11A is a flow diagram illustrating the process for string graph assembly of polyploid genomes performed by the diploid contig generator 114 according to an exemplary embodiment. The process may begin by the receiving a string graph and an untig graph generated from sequence reads of at least 0.5 kb, more preferably of at least 1 kb in length (block 1100). In accordance with the exemplary embodiments, rather than identifying only non-branching simple paths in the unitig graph, the diploid contig generator 114 uses long reads to generate the string graph from which the unitig graph is constructed. In one embodiment, the unitig graph may be generated by the string graph generator 112. Alternatively, the unitig graph may be generated by the diploid contig generator 114.

String bundles are identified in the unitig graph or the string graph (block 1102). In one embodiment, a string bundle may comprise a set of non-branching edges that form compound paths that may contain sequences from both haplotypes. Each of the identified string bundles is then processed as described below. Block 1102 may include two sub-steps.

First, a primary contig is determined from each of the string bundles or the string graph (block 1102A). In one embodiment, a primary contig 1102 is a single path without branching that extends the length of the unitig graph or the string graph. The primary contig may represent a single template molecule, or may represent more than one homologous template molecule, at least in regions where the homologs do not differ in sequence.

Next, associated contigs that contain structural variations and other SNPs or mutation (which can be determined by an aligner) compared to the primary contig are determined (block 1102B). In one embodiment, associated contigs are paths in parallel to the primary contig in bubble regions of the string bundle. For example, in diploid samples, associated contigs often represent regions in which the homologous templates comprise sequence differences, e.g., SNPs, structural variations, mutations, etc.

In further embodiment, the process may further include identifying candidate break points in the primary contigs; and breaking the corresponding primary contigs at the break points. The above steps are described in further detail below.

According to one aspect of the exemplary embodiment, there are two embodiments for identifying the string bundles. In the first embodiment, a single path through the unitig graph is used to find a primary path through the unitig graph that is used to define a string bundle as well as a primary contig. Paths that branch from the primary contig and then rejoin the primary contig may be designated as associated contigs and are used to define bubble regions of the string bundle.

In the second embodiment for identifying string bundles, bubble regions are first identified as compound paths in the string graph, which means that this implementation is not constrained by first attempting to find one path through the graph. A new unitig graph is then generated in which each of the compound paths is replaced by a compound edge and each set of simple paths connecting a pair of compound paths in the original unitig graph are replaced in the new unitig graph with a simple edge. This new unitig graph is used to find the primary and associated contigs.

Embodiment 1

Identifying String Bundles and Determining Primary and Associated Contigs

Figure 11B:
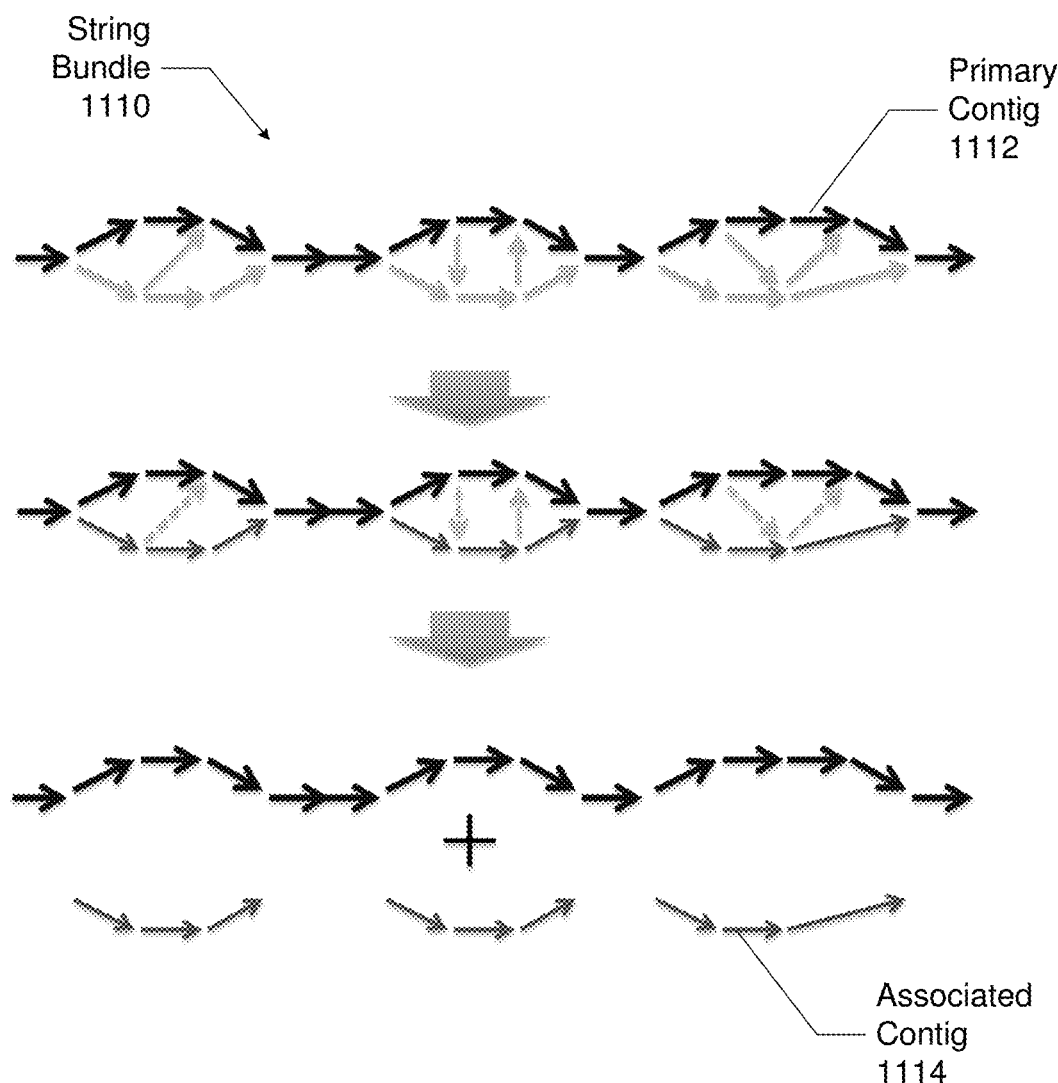
FIG. 11B is a diagram graph illustrating the processing of string bundles, which comprise bubbles as well as "non-bubble" portions.

FIG. 11B is a diagram graph illustrating the processing of string bundles, which comprise bubbles as well as "non-bubble" portions. The process may include analyzing each of the string bundles 1110 to determine a primary contig 1112 for each string bundle 1110 (FIG. 11A, block 1102A). In one embodiment determining the primary contig comprises assigning edges in the corresponding string bundle to the primary contig that form a contiguous, end-to-end "best path" sequence that extends the a length of the string bundle. Consequently, a primary contig is a path through a string bundle that explains most of the read overlaps and may represent the sequence of a particular strand of the sample nucleic acid used to generate the sequence read data. Rules for traversing the graph to find the best paths for the contigs can be determined by the ordinary practitioner based on well-established statistical models and methods.

Associated contigs 1104 that comprise structural variations and other variations which the overlapper can detect as compared to the primary contigs 1102 are also determined (FIG. 11A, block 1102B). As shown FIG. 11B, in one embodiment determining the associated contigs comprises assigning edges in paths parallel to the primary contig 1112 in bubble regions of the string bundle 1110 as the associated contigs. In one embodiment, associated contigs 1114 may represent sequences that differ between two homologous sequences. The associated contigs 1114 may be constructed iteratively along the path of the corresponding primary contig 1112, and the process continues until every edge in the string bundle 1110 is associated with either one of the primary contigs 1112 or one of the associated contigs 1114. The result of this process is that the string bundle 1110 comprises the primary contigs 1112 plus the locally associated contigs 1114.

In operation, the contigs in each of the string bundles 1110 are analyzed to distinguish junctions in the respective string bundles caused by the presence of homologous regions having structural variations from those that indicate true branching paths, e.g., caused by the presence of repeat sequences 904 within a nucleic acid sequence. The contigs are analyzed to identify candidate branch points in the primary contigs 1112. The primary contigs are broken at these branch points to provide corrected primary contigs 1112 along with their locally associated contigs 1114.

One aspect of the exemplary embodiments is the recognition of the importance of distinguishing a junction in a unitig graph as a vertex belonging to a string bundle or a vertex of a branching path from which a primary contig 1112 and associated contigs 1114 diverge. Consequently, the diploid contig generator 114 determines whether the vertex is indicative of minor structural variation between two homologous sequences that can remain within the string bundle, or indicative of a major structural topology resulting in a branching path that cannot remain within the string bundle and requires the assembly be broken at that point.

Figure 12A:
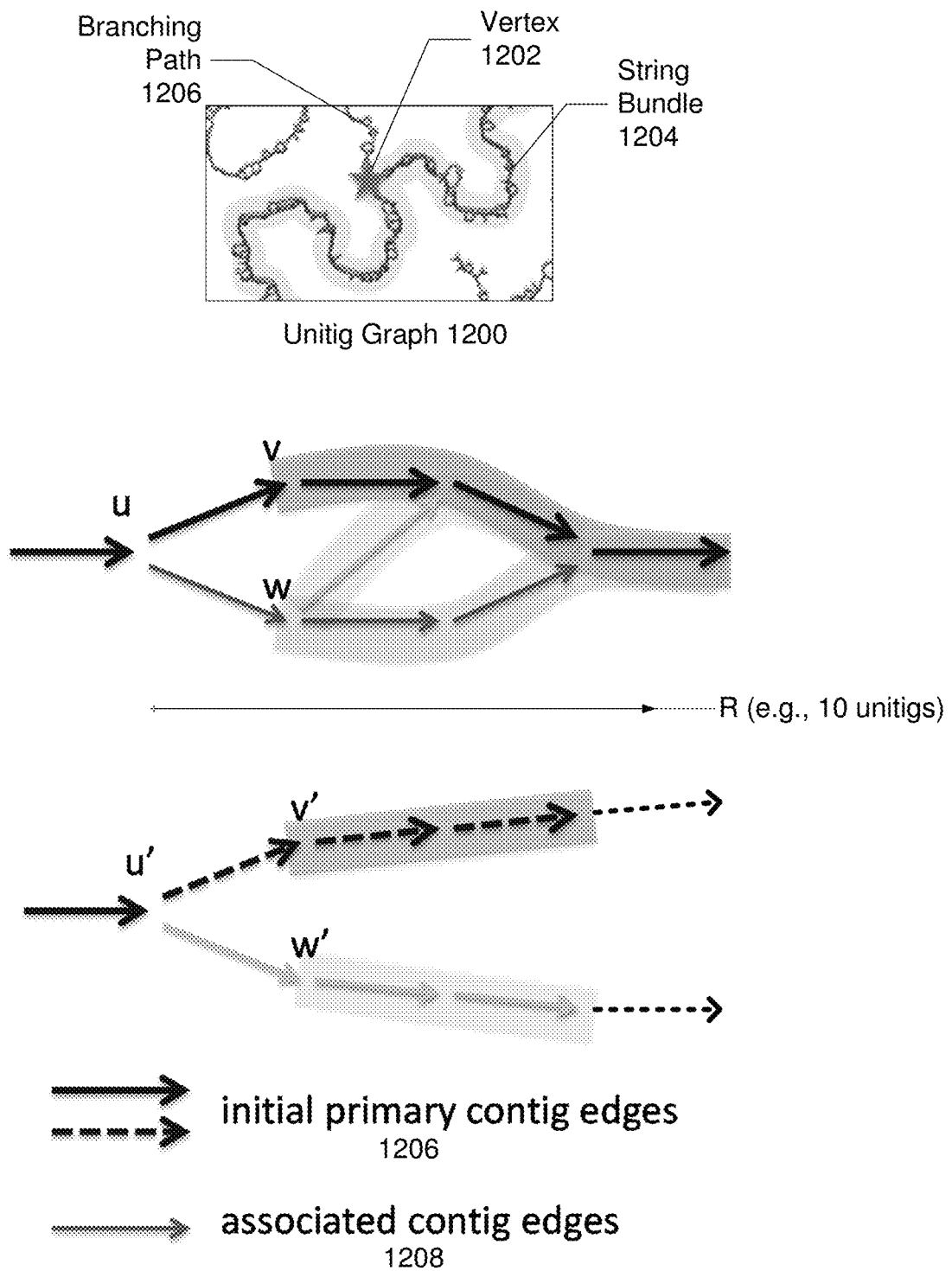
FIG. 12A is a diagram illustrating a process for determining whether a junction at a vertex in a unitig graph belongs to a string bundle or a branching path.

FIG. 12A is a diagram illustrating a process for determining whether a junction at vertex 1202 in a unitig graph 1200 belongs to a string bundle 1204 or is indicative of a branching path 1206. In one embodiment, this may be accomplished by analyzing a distance at which two downstream paths of a vertex rejoin, where one of the paths may define a primary contig 1208 and the other path may define a candidate associated contig 1210. For example, given a junction at vertex U, and two downstream paths V and W, it is determined whether V and W meet within a predefined radius R from the vertex U. If the two downstream paths (e.g., V and W) rejoin within a predefined radius, then the two paths are identified as part of a single string bundle 1204.

However, at vertex U', if the downstream paths V' and W' do not rejoin within the predefined radius R, the string bundle 1204 is broken at that junction, e.g., caused by repeats, and the associated contig for the branching path is discarded and not included in the string bundle 1204.

In one embodiment, the radius is a selectable parameter that may be tunable by the operator, as it depends on the genome structure. As a point of reference, however, the radius may be approximately 10 base calls in length in the EXAMPLE above. In one embodiment, the radius may be selected prior to assembly based on known characteristics (e.g., size) of structural variations in the sample nucleic acids. More specifically, the length of the radius should be selected to so that the bubbles fully contain the structural variations and allow the two downstream paths of the bubble to rejoin within the radius to avoid breaking the bundle. In addition, after assembly, the results can be used to determine a radius for a subsequently performed assembly. In particular, if the contigs resulting from the assembly are shorter than desired resulting in an overly fragmented assembly, the radius can be increased and the assembly process re-run to try to increase the contig lengths in the final assembly. In an alternative embodiment, if the final assembly seems to contain repeat regions that were not correctly identified as branching points and created mis-assemblies, then a radius of a shorter length may be selected.

Although in the exemplary embodiment, the string bundle is broken at the branch points after the primary contigs and the associated contigs are determined, in an alternative embodiment, the string bundle may be broken at the branch points at an earlier stage during processing.

Embodiment 2

Identifying String Bundles and Determining Primary and Associated Contigs

Figure 12B:
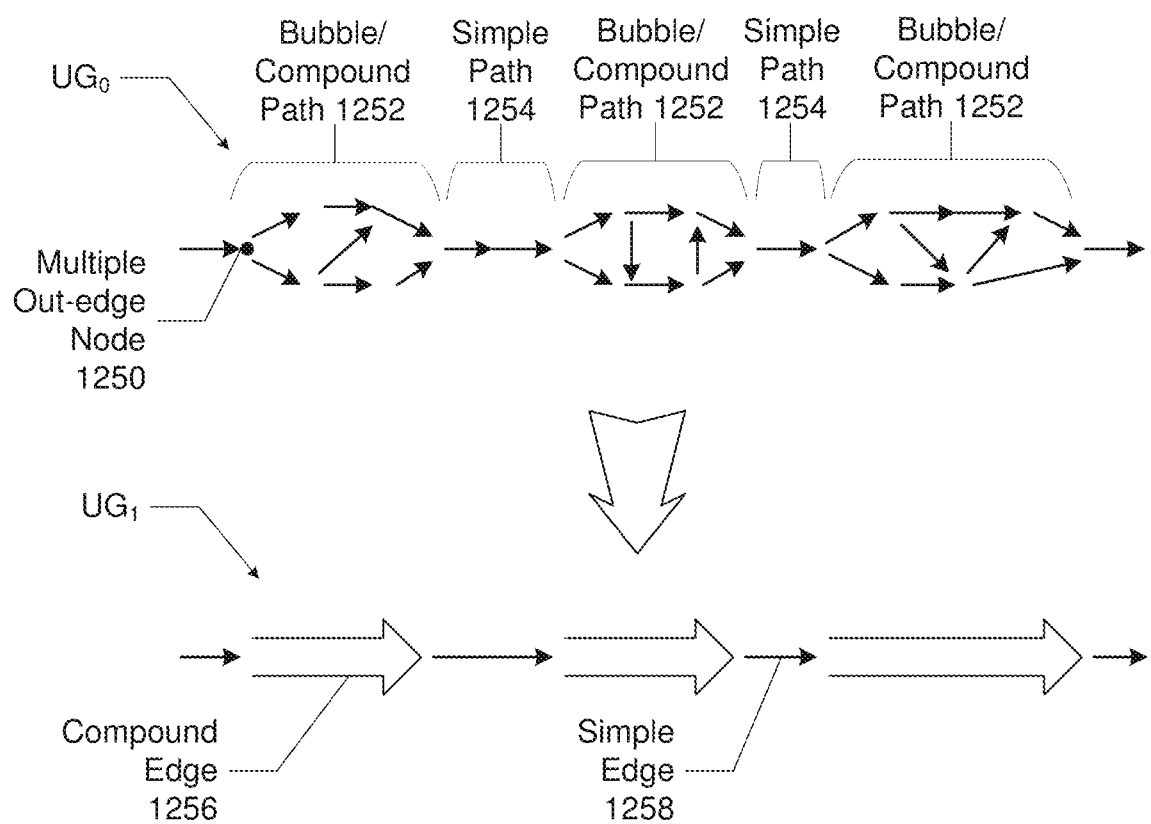
FIG. 12B is a diagram graph illustrating the processing of string bundles according to a second embodiment.

FIG. 12B is a diagram graph illustrating the processing of string bundles according to a second embodiment. In the second embodiment for identifying string bundles and determining primary and associated contigs, the goal is to first identify bubble regions as compound paths. One purpose of this is to attempt to decompose the string graph into simple paths and simple bubbles. However, the string graph for a diploid genome with complicated heterozyguous structure variations or repeat structures may not be easy to decompose into simple path and simple bubbles due to possible subgraph motifs.

For example, it is possible to have nested bubbles, loops, tangled bubbles, and long branches between a source node and a sink node, in which case, the bubbles may be caused some repeats at the branching point rather than local structure variation between the haplotypes. The following is one approach for solving this problem.

In Step 1, the initial string graph is simplified to a graph $UG_0$, for example, having simple paths in which edges in a path without any branching node represented with single edge.

In step 2, nodes 1250 having multiple out-edges in $UG_0$ are found and for each of these nodes, a search is initiated to find a local "bundle" of edges. During this search, tracers, or labels, are assigned to the nodes 1250 having multiple out-edges to trace down each branch from a source node to a sink node. An assigned tracer may be active or inactive. Finding the local bundles of edges includes the following sub-steps.

1. For each branch iteration step, each node having an active tracer is checked to determine if all in-nodes of that node have assigned tracers. If so then active tracers are assigned to all offspring nodes and the tracer of the parent node is made inactive. If there is only on active tracer left, all traced nodes and edges between them are designated as a compound path 1252.
2. Loops are detected in response to determining that any offspring node of a parent node that has an active tracer already has an assigned tracer. When a loop is detected, the search stops and no compound path is generated.
3. In some complicated repetitive parts of the genome, the number of active tracer can increase quickly. Therefore, only a predefined number of active tracers are assigned. The searches stopped when the number of active tracers assigned exceeds the predefined number.
4. For each step, the number of nodes and the length of the paths are calculated as number of sequence bases from the source node to all nodes with active tracers. The search is stopped when the number of nodes and the length of exceed predefined threshold.

In step 3, for compound paths 1252 that are overlapped with others, or for nested compound paths (e.g., a smaller compound path is part of a larger compound path), the longest compound path is selected and the smaller compound path ignored.

In step 4, a new unitig graph $UG_1$ is generated in which each of the compound paths 1252 identified in $UG_0$, are replaced by a single compound edge 1256; and each the simple path 1254 in $UG_0$ connecting the compound paths 1252 are replaced with a simple edge 1258. The resulting unitig graph $UG_1$ contains compound edges 1256 connected by simple edges 1258 and is used to identify the string bundles, primary contig and associated contigs, as described above.

The result of the above processing is a string bundle 1204 comprising corrected primary contigs 122 along with their locally associated contigs 124 (FIG. 1). The output from the diploid contig generator 114 may include the primary contigs 122, the associated contigs 124, and/or a fused assembly graph 126 that comprises the primary and associated contigs.

Figure 13:
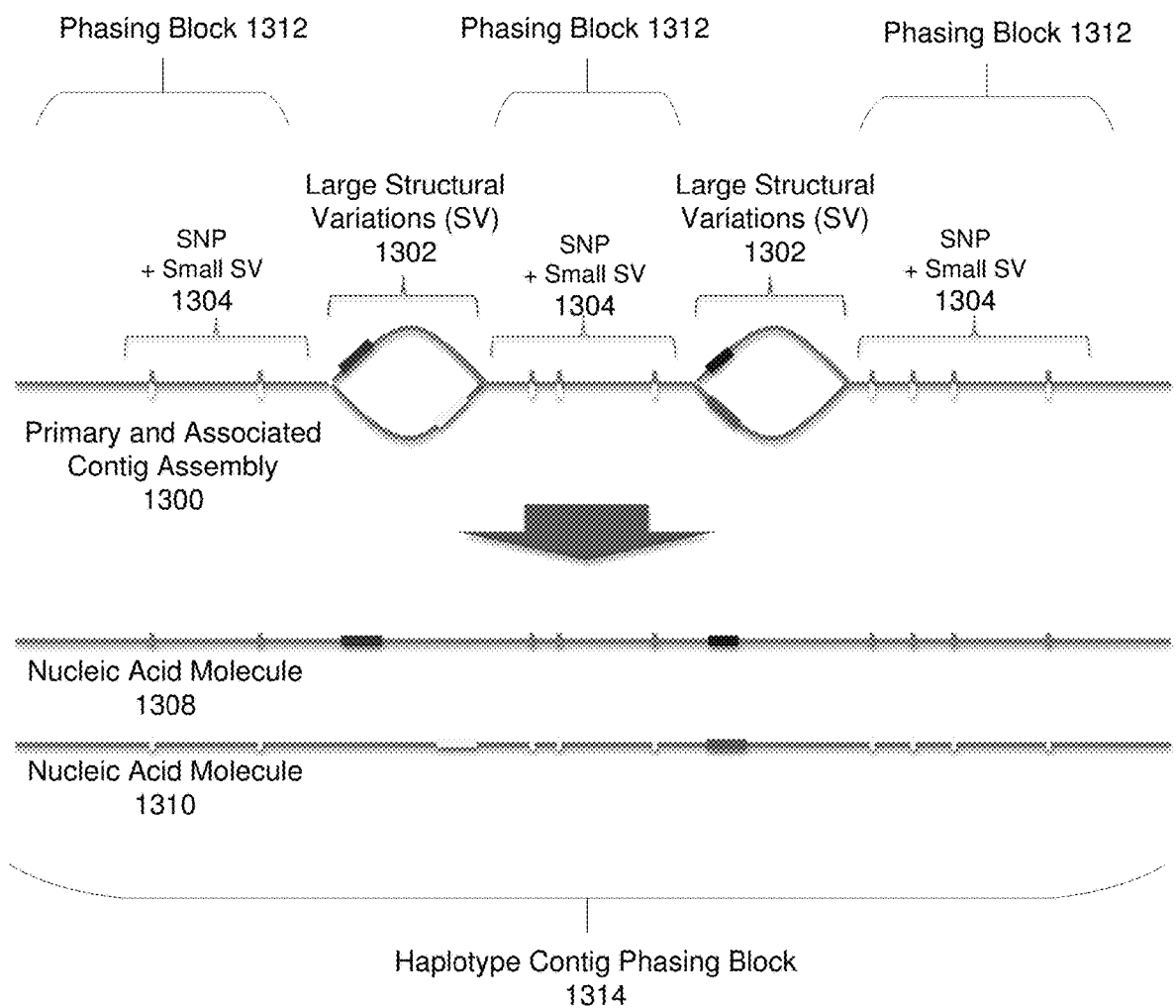
FIG. 13 is a diagram graphically illustrating construction of a final consensus sequence based on the primary contigs and the associated contigs.

FIG. 13 is a diagram graphically illustrating construction of a final consensus sequence based on the primary contigs and the associated contigs. A primary and associated contig assembly 1300 is shown including large structural variations (SV) 1302 (shown as rectangles) and also single-nucleotide polymorphisms (SNPs) and small SVs 1304. Two of the large SVs 1302 belong to one nucleic acid molecule 1308 and the other two large SVs 1302 belong to another nucleic acid molecule 1310. This provides the general structure that needs to be resolved to provide the sequences for the individual sample nucleic acid molecules 1308 and 1310, e.g., two homologous chromosomes.

Referring again to FIG. 3A, according to a further aspect of exemplary an embodiment, after the fused assembly graph is generated from both haplotypes (block 200), the haplotype graph generator 117 and the haplotype graph merger and haplotig segregator 119 apply logic to determine which alleles go together in a single nucleic acid to provide the haplotype for that molecule in order to phase both structural variations and SNPs. This may be accomplished by examining the allelic constitution of the sequence reads 116 (FIG. 1) to determine whether a single sequence read contains more than one of these variant positions (large SVs or SNPs). When it is determined that a single read (which is necessarily from a single molecule) comprises loci for more than one of the variant positions, the alleles at those loci are identified as linked, originating from a single original nucleic acid molecule. Once the allelic constitution of the long sequence reads 116 has been determined with respect to the primary and associated contig assembly 1300, it can be determined which version of each variant position originates with which nucleic acid molecule 1308 and 1310, and thereby determine the final consensus sequence for the original nucleic acid molecules.

In FIG. 13, all the alleles for one strand are shown on the top of the primary and associated contig assembly 1300, and all the alleles for the other strand were shown on the bottom, but the source of each allele isn't actually known. According to a further aspect of the exemplary embodiments, the haplotype graph generator 117 and the haplotype graph merger &haplotig segregator 119 examine information associated with the long sequence reads 116 to determine which alleles go together on which haplotype.

As described in FIGS. 2 and 3A, this includes generating haplotype-specific assembly graphs using phased reads and haplotype aware overlapping of the phased reads (block 202), resulting in haplotype-specific assembly graphs 203. The fused assembly graph 201 and haplotype-specific assembly graphs 203 are merged (block 204) to generate a merged assembly haplotype graph 205. Cross-phasing edges are removed from the merged assembly haplotype graph 205 to generate a final haplotype-resolved assembly graph 207 (block 206). Haplotype-specific haplotigs are then reconstructed from the final haplotype-resolved assembly graph 207, resulting in haplotype-specific contigs 209 with connected phasing blocks.

The process of generating the haplotype-specific assembly graphs using by phasing reads and using a haplotype aware overlapping process (block 202) will now be explained. The process may include, for each haplotype-fused contig, identifying a subset of raw reads that belong to that haplotype-fused contig (block 311). Next, the reads are phased (block 313), which sorts the reads into groups representing different haplotypes using SNP information. Finally, an unzipping of the haplotype-fused contig 319 to a haplotype-specific contigs is performed.

In one embodiment, identifying the subset of raw reads that belong to a haplotype-fused contig may be performed by collecting the reads originating from the same genomic region of a contig using the overlapping data for generating the assembly, followed by phasing the reads from the same contig by block and phase, which requires two indexes. For a human, for example, the process will result in approximately 5000 contigs, and this process may partition the initial reads into approximately 5000 bins corresponding to the contigs. However, during targeting sequencing where all the reads originate from one region, the number of contigs may be significantly less.

Referring again to FIG. 13, regions of the contigs where the SNPs can be associated into haplotypes unambiguously determined by a statistics method are called phasing blocks 1312. Each phasing block 1312 has two different phases, phase 0 and phase 1, corresponding to the two different haplotypes. During partitioning, all the reads identified as belonging to a single contig are assigned to a particular block, and later in the process the reads will be assigned to one of the phases. Each nucleic acid molecule 1308 and 1310, or haplotype, represents a region where all the SNPs are phased to one another, and are referred to here as a haplotype contig phasing block 1314. According to the exemplary embodiments, information pertaining to phasing between SNPs and structural variations are combined to provide de novo diploid genome assembly and haplotype sequence reconstruction.

Referring again to FIG. 3A, phasing the reads (block 313) includes aligning the reads associated with each primary contig by a local alignment 312 process. This process generally includes aligning the reads to a reference sequence. The reference sequence can be a known reference sequence, e.g., from a public database. Alternatively, in certain embodiments the reference sequence is a primary contig from the fused assembly graph. After the reads are aligned, a heterozygous SNP (hetSNP) calls 314 process is performed that identifies SNPs, followed by a phase het-SNPs 316 process, which groups the reads having shared SNPS.

Figure 14:
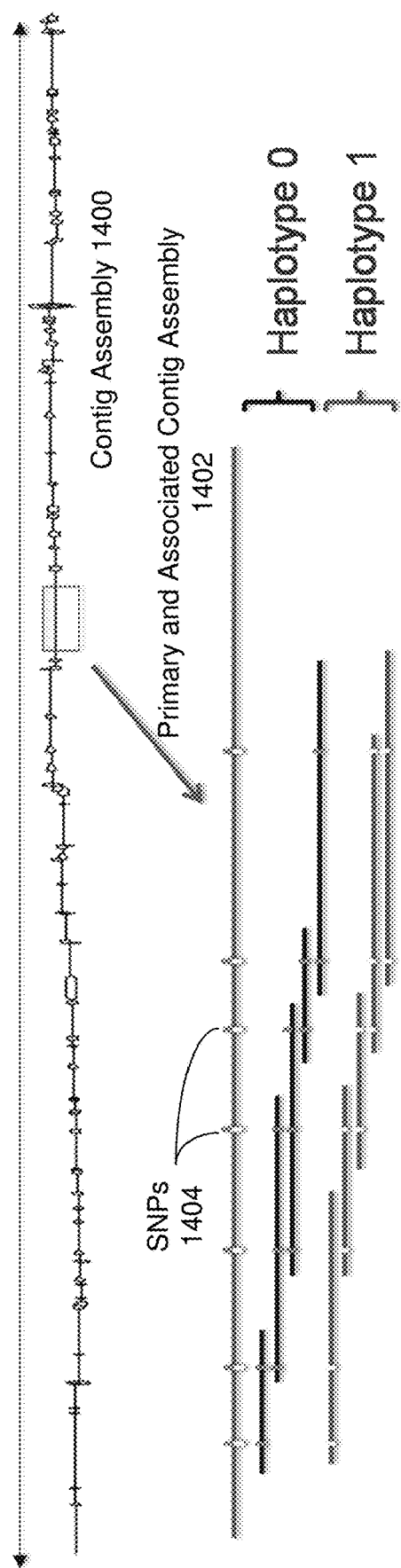
FIG. 14 is a graphic example showing an example of phasing SNPs and reads through higher identity regions.

FIG. 14 is a graphic example showing an example of phasing SNPs and reads through higher identity regions. This particular example shows a portion of a 9 Mbp contig assembly 1400 spanning through the MHC region of a diploid human genome. Conceptually, the contig assembly 1400 contains bubbles mixed in with linear paths. In the linear path, some type of marker or signal may be used to separate the reads into different groups representing different haplotypes. In one embodiment, SNPs are used as the marker or signal, although in another embodiment, other markers or signals may be used such as kinetic information associated with the reads. For example, even though read sequences may be very similar, kinetic information that reflect molecule level difference, e.g., methlythation, may be used to identify a set of reads that have characteristics indicating modified bases to show that the modified bases should be associated with one haplotype or another.

In this process the heterozygous SNPs are identified de novo using the primary contig as a reference, and the reads are aligned to this reference. Any SNPs identified are phased to determine which alleles (indicated by the variant SNPs) exist together on the same chromosome based upon their presence within a single read. Overlapping reads that overlap at least one SNP and further comprise at least one SNP outside of the overlapping region are used to link SNP alleles that are in different reads. In FIG. 14, all the alleles/SNPs 1404 for one haplotype are shown on the top of the primary and associated contig assembly 1402, and all the alleles for the other haplotype are shown on the bottom. Using the phased SNPs 1404, the reads may be compared to those SNP locations. If a read contains an SNP in haplotype 1, then the read is associated with haplotype 1. By phasing the SNPs 1404, the reads containing those SNPs 1404 may also be phased according to haplotype, as shown By grouping the SNPs and reads simultaneously, information about which read belongs to the same block in the same phase is obtained, producing a set of phased reads 318 that can be used to reconstruct haplotypes different by only small variations, e.g., 1 to 6%.

Referring again to FIG. 3A, after the reads are phased, the sequence aligner/overlapper 110 (or some other component) performs phase-specific assembly, referred to herein as unzipping the contigs (block 319). When unzipping the contig, the sequence aligner/overlapper 110 aligns (block 320) the sequencing reads to identify regions of similarity between the sequences. The aligned sequences are then error corrected (block 322) to obtain a set of error-corrected reads, and the error-corrected reads are aligned (block 324). This process is similar to the steps used to generate the fused assembly graph assembly from both haplotypes except during the overlap stage (block 326), the phased reads 318 are used to ensure that only the aligned error-corrected reads for the same phase are overlapped with each other (reads that are contained within other overlapping reads are discarded). This results in a set of overlapping reads for each haplotype, which are then used by the haplotype graph generator 117 to generate haplotype-specific string graphs (block 328). The unzipping process may include blocks 320-326, 328 and 204-206.

Figure 15:
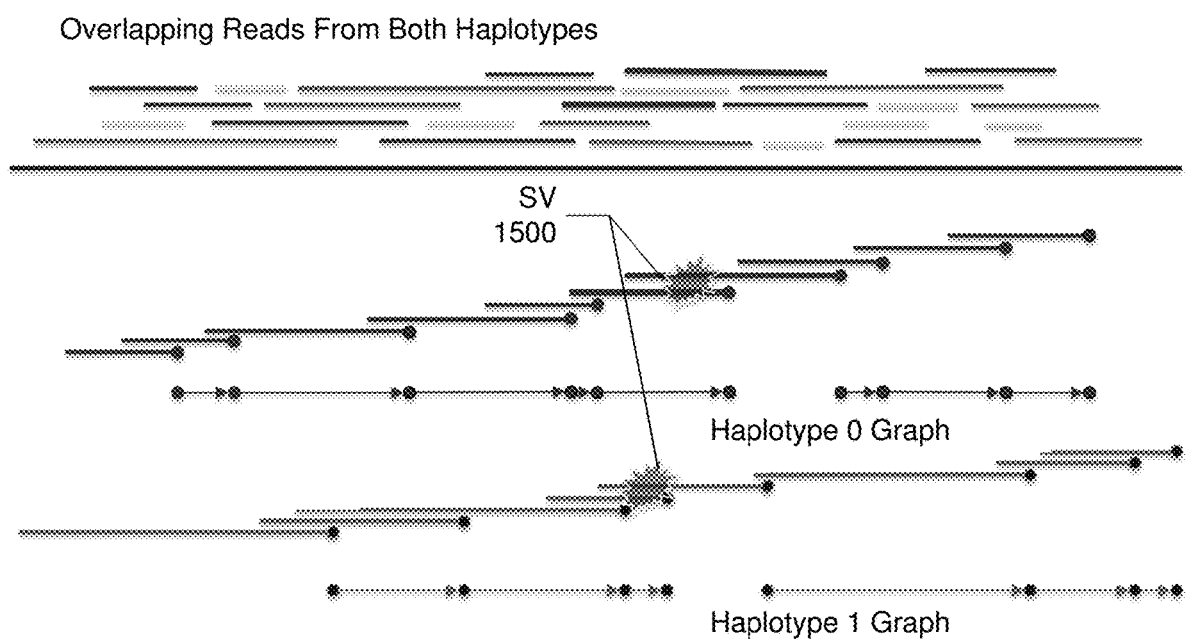
FIG. 15 is a diagram illustrating the haplotype-specific assembly graphs generated by string graph generation.

FIG. 15 is a diagram illustrating the haplotype-specific assembly graphs generated by string graph generation 328. Overlapping reads from both haplotypes have been separated into groups according to haplotypes. String graph generation 328 then generates separate haplotype graphs, haplotype 0 graph and haplotype 1 graph. Structural variations 1500 found in each set of reads typically stops extension of contigs around the nodes of such complex bubbles in the graph and only non-branching simple paths are identified because the conventional methods do not analyze the large scale string graph structure. Consequently, simply separating the reads into groups according to haplotypes and performing assembly for each of the haplotypes creates breaks in the graphs for the two haplotypes where divergent paths are encountered due to structural variations 1502, resulting in in a fragmented assembly for the haplotype 0 graph and the haplotype 1 graph. SV 1500 is one example where the SNP phasing may be ineffective and the phasing block might break. Another example is if there is high homologous region between the haplotypes where the SNPs density is so low that they can't be linked by the reads, the haplotype contigs will break too also resulting in fragmented haplotype graphs.

Referring again to FIGS. 2 and 3A, after the haplotype-specific assembly graphs are generated, the fused assembly graph and the haplotype-specific assembly graphs are merged by the haplotype graph merger & haplotig segregator 119 during the merged graphs process (block 204) to increase graph continuity and provide full resolution.

Figure 16:
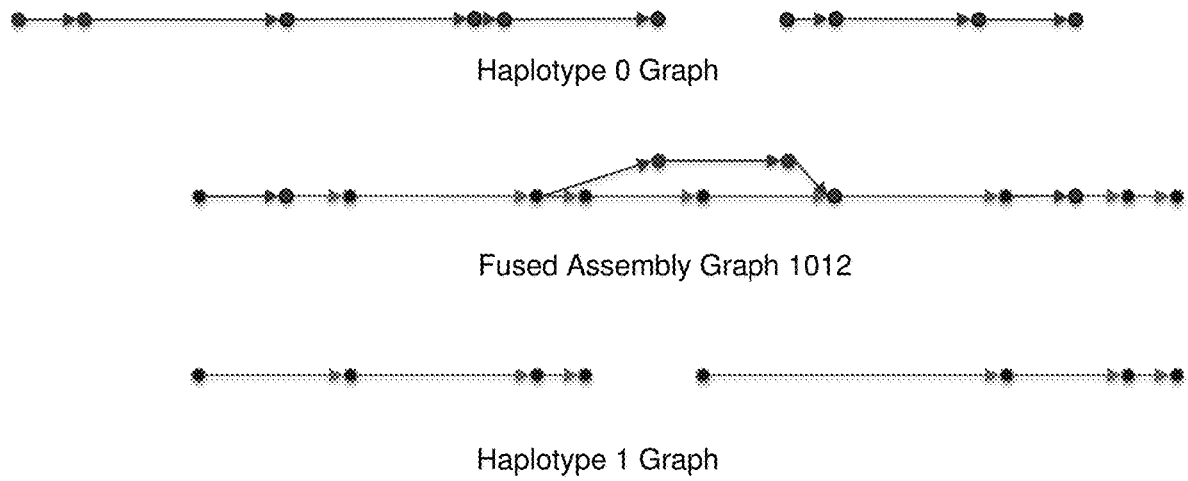
FIG. 16 is a diagram illustrating the fused assembly graph and the haplotype-specific assembly graphs.

FIG. 16 is a diagram illustrating the fused assembly graph 1012 and the haplotype-specific assembly graphs, haplotype 0 graph and the haplotype 1 graph, that are input to the haplotype graph merger and haplotig segregator 119.

Figure 17:
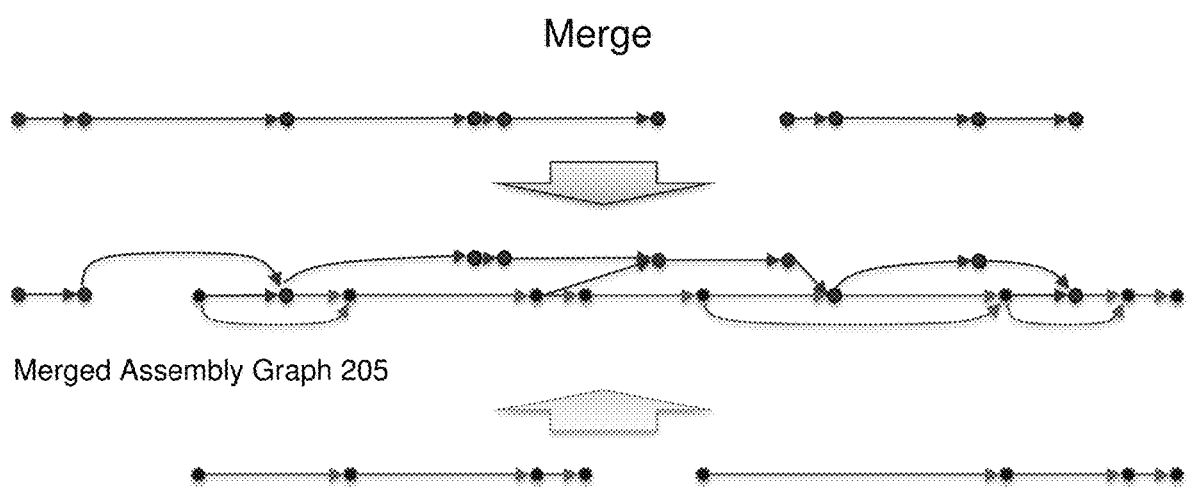
FIG. 17 is a diagram illustrating the merging of the fused assembly graph and the haplotype-specific assembly graphs.

FIG. 17 is a diagram illustrating the merging of the fused assembly graph 1012 and the haplotype-specific assembly graphs (block 204) to generate the merged assembly haplotype graph 205. The merged assembly haplotype graph 205 includes some new nodes and some new edges, and contains information from the original three graphs, some of which may be discarded at this point. Some edges in the graph connect the nodes from the same haplotype, and others connect the nodes from different haplotypes, which are cross-phased edges.

Referring again to FIGS. 2 and 3A, after the merged assembly haplotype graph 205 is generated, cross-phasing edges are removed from the merged assembly haplotype graph 205 (block 206) to generate the final haplotype-resolved assembly graph 207.

Figure 18:
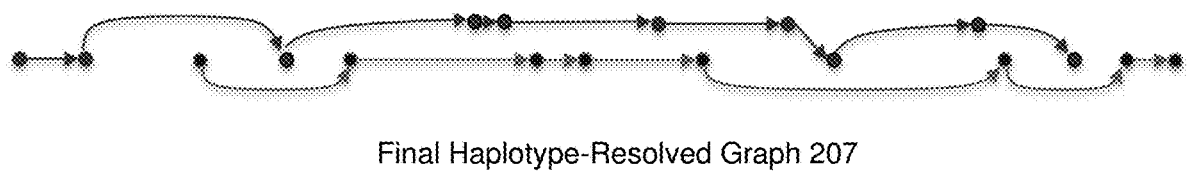
FIG. 18 is a diagram illustrating removal of the cross-facing edges from the merged assembly haplotype graph to generate the final haplotype-resolved assembly graph.

FIG. 18 is a diagram illustrating removal of the cross-facing edges from the merged assembly haplotype graph to generate the final haplotype-resolved assembly graph 207, leaving two distinct paths corresponding to each haplotype. Comparing the final haplotype-resolved assembly graph 207 shown in FIG. 18 to the original haplotype-specific assembly graphs and fused assembly graph shown in FIG. 16, it can be seen that the paths in final haplotype-resolved assembly graph 207 continue through the initial break and branch points shown in three original graphs in FIG. 16.

In one embodiment, the process of creating the merged assembly haplotype graph 205 and removing the cross-facing edges may be performed as two separate processes, as shown in FIG. 2, or alternatively as one process as shown in FIG. 3A.

Referring again to FIGS. 2 and 3A, after the final haplotype-resolved assembly graph 207 is generated, haplotype-specific contigs, referred to herein as haplotigs, are generated from the final haplotype-resolved assembly graph (block 208) with structural variations and SNPs. In one embodiment, the haplotigs may include connected phasing blocks.

Figure 19:
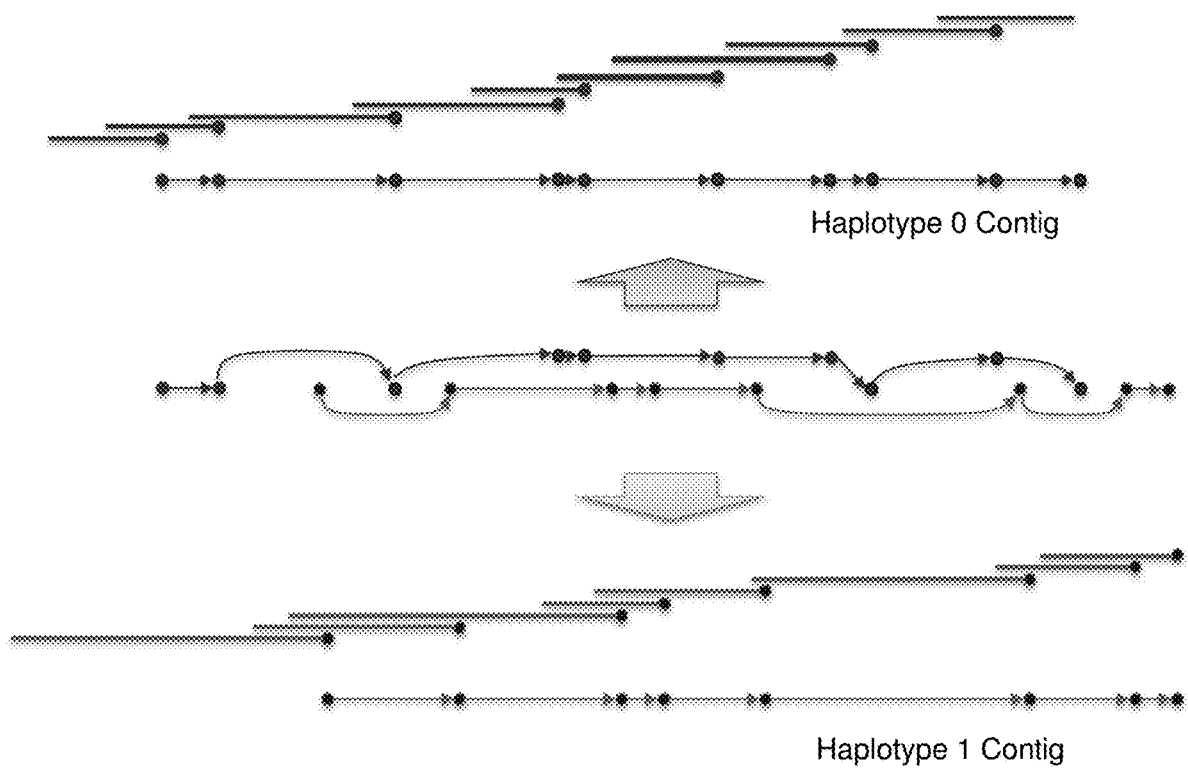
FIG. 19 is a diagram illustrating generation of haplotigs from the final haplotype-resolved assembly graph.

FIG. 19 is a diagram illustrating generation of the haplotigs, haplotype 0 contig and haplotype 1 contig, from the final haplotype-resolved assembly graph 207. The haplotigs connect SNPs using phasing blocks 1312 and connect the SNP phasing blocks 1312 to the structural variations 1302 to create a haplotype contig phasing block 1314, as shown in FIG. 13. Results of the methods and systems disclosed herein may be used for consensus sequence determination from biomolecule sequence data.

Referring again to FIGS. 2 and 3A, for example, an optional final step may be to input the phased reads 318 and haplotype-specific contigs to a haplotype-specific consensus calling process 330. Since it is known which reads correspond to which haplotype, and the reads belong to different phasing blocks, the haplotype-specific consensus calling process 330 should obtain the best accuracy for each haplotype.

Processing blocks 202, 204, 206, and 208 may be performed on each contig generated by the string graph generator 112. In another embodiment, all contigs may be processed at once instead of one by one.

Figure 20:
FIG. 20 is a diagram illustrating possible output options of the de novo diploid genome assembly and haplotype sequence reconstruction process.
Figure 20:
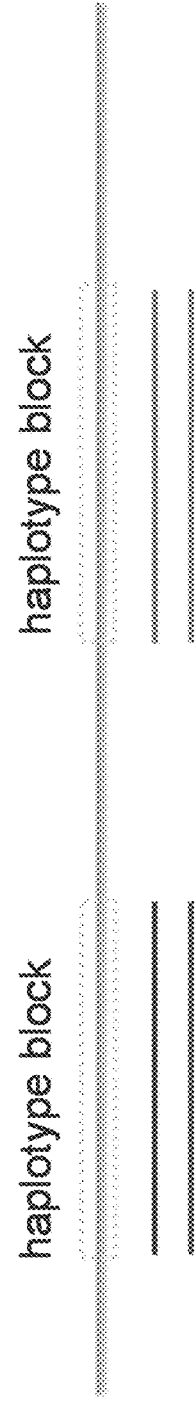
Figure 20:
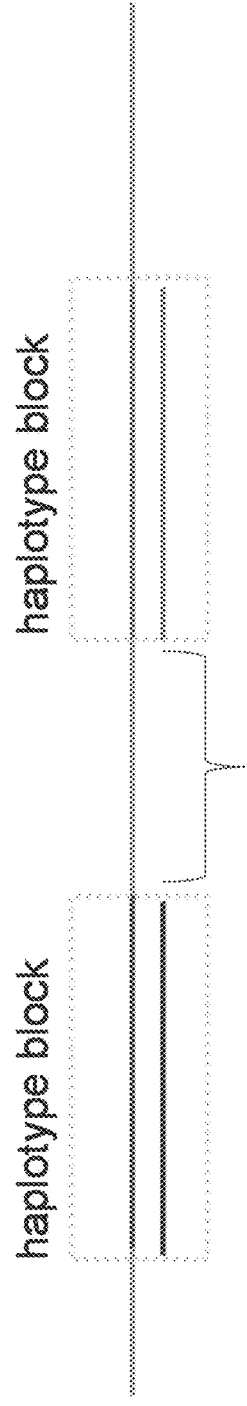

FIG. 20 is a diagram illustrating possible output options of the de novo diploid genome assembly and haplotype sequence reconstruction process. In one embodiment, the output options may include 1) unphased contigs and phase variant calls, 2) unphased primary contigs and phased sequences (haplotype blocks), and 3) primary contigs with annotated phase blocks and alternative phased sequences. Any selected output options may be stored or displayed in whole or in part, as determined by the practitioner.

A method has been disclosed for de novo diploid genome assembly and haplotype sequence reconstruction that effectively integrates multiple variant types into comprehensive assembled haplotypes. In some embodiments, the system includes a computer-readable medium operatively coupled to the processor that stores instructions for execution by the processor. The instructions may include one or more of the following: instructions described with respect to FIG. 2 for receiving input of sequence reads (and, optionally, reference sequence information), instructions for constructing pre-assembled reads, instructions for aligning sequence reads, instructions for generating string graphs, instructions for generating unitig graphs, instructions for identifying string bundles, instructions for determining primary contigs, instructions for determining associated contigs, instructions for correcting reads, instructions for generating consensus sequences, instructions for generating haplotype sequences, instructions that compute/store information related to various steps of the method (e.g., edges and nodes in a string graph, overlaps and branch points in a string graph, primary and associated contigs), and instructions that record the results of the method.

In certain aspects, the methods are computer-implemented methods. In certain aspects, the algorithm and/or results (e.g., consensus sequences generated) are stored on computer-readable medium, and/or displayed on a screen or on a paper print-out. In certain aspects, the results are further analyzed, e.g., to identify genetic variants, to identify one or more origins of the sequence information, to identify genomic regions conserved between individuals or species, to determine relatedness between two individuals, to provide an individual with a diagnosis or prognosis, or to provide a health care professional with information useful for determining an appropriate therapeutic strategy for a patient.

Furthermore, the functional aspects of the invention that are implemented on a computer or other logic processing systems or circuits, as will be understood to one of ordinary skill in the art, may be implemented or accomplished using any appropriate implementation environment or programming language, such as C, C++, Cobol, Pascal, Java, Javascript, HTML, XML, dHTML, assembly or machine code programming, RTL, python, scala, perl, etc.

In certain embodiments, the computer-readable media may comprise any combination of a hard drive, auxiliary memory, external memory, server, database, portable memory device (CD-ft DVD, ZIP disk, flash memory cards, etc.), and the like.

In some aspects, the invention includes an article of manufacture for diploid genome assembly and haplotype sequence reconstruction that includes a machine-readable medium containing one or more programs which when executed implement the steps of the invention as described herein.

EXAMPLE

The methods described herein were used to perform sequence analysis of the 120 Mb *Arabidopsis* genome. The strategy comprised generating a "synthetic" diploid dataset by using two inbred strains of *Arabidopsis*, Ler-0 and Col-0. The two strains were sequenced separately, then sequencing reads generated for each were pooled and subjected to pre-assembly followed by the string graph diploid assembly strategy described herein to determine if this strategy could correctly assemble the two strains from the pooled read data.

After pre-assembly, the sequence reads used as input in the diploid assembly process ranged from about 10 kb to about 22 kb, with the majority of the reads between 10 and 15 kb. The unitig graph shown in FIG. 10A was constructed from a string graph generated using the pooled sequencing reads. The next step was to find an end-to-end path though the unitig graph along which a string bundle could be built. The compound paths of the string bundle contained sequences from both "haplotypes" (in this case, both strains). The string bundle comprised a primary contig and the locally associated contigs, where the primary contig is the path from the beginning to the end of the string bundle that explains most of the overlaps, and the associated contigs are the paths in parallel to the primary contig in the bubbles present in the string bundle. The process was continued until there were no edges left, and the string bundle was subsequently broken at branching points believed to be caused by repeats to provide corrected primary contigs and locally associated contigs.

Finally, vertices in the string bundle were distinguished from those at branching points. Specifically, for vertices that had downstream paths that met within a radius, those downstream paths were kept within the bundle. Vertices that had downstream paths that did not meet within that predefined radius were indicative of a branching point, and the primary contig was broken at those vertices. Data for the resulting assemblies is provided in U.S. provisional application No. 61/917,777, filed Dec. 18, 2013, and incorporated herein by reference in its entirety for all purposes.

It is to be understood that the above description is intended to be illustrative and not restrictive. It readily should be apparent to one skilled in the art that various modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. Throughout the disclosure various references, patents, patent applications, and publications are cited. Unless otherwise indicated, each is hereby incorporated by reference in its entirety for all purposes. All publications mentioned herein are cited for the purpose of describing and disclosing reagents, methodologies and concepts that may be used in connection with the present invention. Nothing herein is to be construed as an admission that these references are prior art in relation to the inventions described herein.

What is claimed is:

1. A method for diploid genome assembly and haplotype sequence reconstruction of at least 120 megabase pairs of a diploid genome, the method comprising:

obtaining a diploid genomic sample comprising a pair of haplotypes;

sequencing the diploid genomic sample to generate a plurality of sequence reads from the diploid genomic sample, wherein the plurality of sequence reads includes sequence reads from both haplotypes in the pair of haplotypes and wherein the plurality of sequence reads collectively encompass at least 120 megabase pairs of the diploid genome;

inputting the plurality of sequence reads, in electronic form, into a computer system comprising a processor coupled to a non-transitory memory to perform a procedure comprising:

generating a fused assembly graph from sequence reads, in the plurality of sequence reads, of both haplotypes in the pair of haplotypes, the fused assembly graph comprised of a plurality of haplotype-fused contigs including identified primary contigs and associated contigs;

generating a plurality of haplotype-specific assembly graphs using phased reads and haplotype aware overlapping of the phased reads;

merging the fused assembly graph and haplotype-specific assembly graphs to generate a merged assembly haplotype graph;

removing one or more cross-phasing edges from the merged assembly haplotype graph to generate a final haplotype-resolved assembly graph; and reconstructing haplotype-specific contigs from the final haplotype-resolved assembly graph resulting in haplotype-specific contigs of at least 120 megabase pairs of the diploid genome for the diploid genomic sample;

wherein generating the plurality of haplotype-specific assembly graphs using phased reads and haplotype aware overlapping of the phased reads further comprises:

for each respective haplotype-fused contig in the plurality of haplotype-fused configs, identifying a subset of raw sequence reads in the plurality of sequence reads that belong to the respective haplotype-fused contig;
phasing the sequence reads to sort the sequence reads into groups representing different haplotypes using single nucleotide polymorphism (SNP) information; and
phasing the sequence reads from the same contig by block and phase.

2. The method of claim 1, wherein generating the haplotype-specific assembly graphs using phased reads and haplotype aware overlapping of the phased reads, further comprises:
unzipping the haplotype-fused contigs to haplotype-specific contigs.

3. The method of claim 1, wherein identifying the subset of raw sequence reads that belong to each haplotype-fused contig, further comprises:
collecting the sequence reads originating from the same genomic region of a contig using the overlapping data for generating the assembly.

4. The method of claim 1, wherein phasing the sequence reads further comprises:
aligning the sequence reads associated with each contig by a local alignment process;
performing a heterozygous SNP (hetSNP) calls process that identifies SNPs; and
performing a phase hetSNPs process that groups the sequence reads having shared SNPS.

5. The method of claim 1, further comprising: grouping SNPs and sequence reads simultaneously to obtain information about which sequence read belongs to a same block in the same phase to produce a set of phased sequence reads that are used to reconstruct haplotypes different by only small variations.

6. The method of claim 2, wherein unzipping the contig further comprises:
aligning sequence reads to identify regions of similarity between the sequences generating aligned sequences;
error correcting the aligned sequences to generate error-corrected sequence reads;
aligning the error-corrected sequence reads; and
using the phased sequence reads during an overlap stage to ensure that only the aligned error-corrected sequence reads for the same phase are overlapped with each other, resulting in a set of overlapping sequence reads for each haplotype.

7. The method of claim 6, further comprising using the set of overlapping sequence reads for each haplotype to generate the plurality of haplotype-specific assembly graphs.

8. The method of claim 1, wherein the merged assembly haplotype graph includes edges that connect nodes from the same haplotype, and edges connecting nodes from different haplotypes, which are cross-phased edges.

9. The method of claim 1, wherein the haplotype-specific contigs include connected phasing blocks.

10. The method of claim 9, wherein generating the fused assembly graph further comprises:
receiving a string graph and a unitig generated from sequence reads, in the plurality of sequence reads, of at least 0.5 kilobases in length;
identifying string bundles in the unitig graph;
determining a primary contig from each of the string bundles; and
determining associated contigs that contain structural variations compared to the primary contig.

11. The method of claim 9, further comprising:
identifying candidate branch points in the primary contigs; and
breaking the corresponding primary contigs at the branch points.

12. The method of claim 9, wherein the sequence reads comprise long sequence reads ranging in length from about 0.5 to about 1 kb, from about 0.5 to about 2 kb, from about 0.5 to about 3 kb, from about 0.5 to about 5 kb, from about 0.5 to about 10 kb, from about 0.5 to about 15 kb, or from about 0.5 to about 20 kb.

13. The method of claim 10, wherein identifying string bundles in the unitig graph further comprises:
traversing the unitig graph to identify a set of edges that form non-branching compound paths.

14. The method of claim 10, wherein determining primary contigs from each of the string bundles further comprises:
assigning edges in the corresponding string bundle to the primary contig that form a contiguous, end-to-end best path sequence that extends a length of the string bundle.

15. The method of claim 14, wherein the associated contigs comprise paths in parallel to the primary contig in the bubble regions of the string bundle.

16. The method of claim 10, wherein determining associated contigs that contain structural variations compared to the primary contigs further comprises:
iteratively constructing associated contigs along a path of a corresponding primary contig until every edge in the string bundle is associated with either one of the primary contigs or one of the associated contigs.

17. The method of claim 10, further comprising: analyzing contigs in each of the string bundles to distinguish junctions in the respective string bundles caused by a presence of homologous regions having structural variations from those caused by repeat sequences.

18. The method of claim 17, further comprising: determining whether a junction at vertex in the unitig graph belongs to a string bundle or a branching path by analyzing a distance at which two downstream paths of the vertex rejoin, where one of the paths defines the primary contig and the other path defines a candidate associated contig.

19. The method of claim 18, further comprising:
responsive to determining that the two downstream paths rejoin within a predefined radius, identifying the two downstream paths as part of a single string bundle; and
responsive to determining that the two downstream paths do not rejoin within a predefined radius, breaking the string bundle at the junction caused by repeats, and discarding the associated contig for the branching path.

20. The method of claim 10, further comprising:
responsive to determining the primary contigs and the associated contigs, examining an allelic constitution of the sequence reads to determine whether a single sequence read contains more than one of variant positions, including bubbles and single nucleotide polymorphisms (SNPs);
responsive to determining that the single read contains more than one of the variant positions and therefore that the alleles at those loci are linked, identifying the loci as originating from a single original nucleic acid molecule; and
determining which version of each variant position originates with which nucleic acid molecule, thereby determining a final consensus sequence for the nucleic acid molecules.

21. The method of claim 10, wherein receiving the string graph further comprises:
pre-assembling sequence reads by alignment and assembly, comprising choosing a best-match sequence read from sequence read data as a seed sequence, followed by aligning remaining reads in the sequence read data to the seed sequence to generate a set of aligned sequences; and
generating the string graph from the aligned sequences.

22. A method for diploid genome assembly and haplotype sequence reconstruction, the method comprising:
obtaining a diploid genomic sample comprising a pair of haplotypes;
sequencing the diploid genomic sample to generate a plurality of sequence reads from the diploid genomic sample, wherein the plurality of sequence reads includes sequence reads from both haplotypes in the pair of haplotypes;
inputting the plurality of sequence reads, in electronic form, into a computer system comprising a processor coupled to a non-transitory memory to perform a procedure comprising:
generating a fused assembly graph from sequence reads, in the plurality of sequence reads, of both haplotypes in the pair of haplotypes, the fused assembly graph comprised of a plurality of haplotype-fused contigs including identified primary contigs and associated contigs, wherein the generating the fused assembly comprises using a string graph generated from the plurality of sequence reads, wherein the string graph comprises at least 9 thousand nodes and comprises at least 9 thousand edges;
generating a plurality of haplotype-specific assembly graphs using phased reads and haplotype aware overlapping of the phased reads;
merging the fused assembly graph and haplotype-specific assembly graphs to generate a merged assembly haplotype graph;
removing one or more cross-phasing edges from the merged assembly haplotype graph to generate a final haplotype-resolved assembly graph; and
reconstructing haplotype-specific contigs from the final haplotype-resolved assembly graph resulting in haplotype-specific contigs for the diploid genomic sample;
wherein generating the plurality of haplotype-specific assembly graphs using phased reads and haplotype aware overlapping of the phased reads further comprises:
for each respective haplotype-fused contig in the plurality of haplotype-fused configs, identifying a subset of raw sequence reads in the plurality of sequence reads that belong to the respective haplotype-fused contig;
phasing the sequence reads to sort the sequence reads into groups representing different haplotypes using single nucleotide polymorphism (SNP) information; and
phasing the sequence reads from the same contig by block and phase.

23. A method for diploid genome assembly and haplotype sequence reconstruction of at least 120 megabase pairs of a diploid genome, the method comprising:
inputting a plurality of sequence reads, in electronic form, that have been obtained by sequencing of a sample of a diploid genome, wherein the plurality of sequence reads collectively encompass at least 120 megabase pairs of the diploid genome, into a computer system comprising a processor coupled to a non-transitory memory to perform a procedure comprising:
generating a fused assembly graph from sequence reads, in the plurality of sequence reads, of both haplotypes in the pair of haplotypes, the fused assembly graph comprised of a plurality of haplotype-fused contigs including identified primary contigs and associated contigs;
generating a plurality of haplotype-specific assembly graphs using phased reads and haplotype aware overlapping of the phased reads;
merging the fused assembly graph and haplotype-specific assembly graphs to generate a merged assembly haplotype graph;
removing one or more cross-phasing edges from the merged assembly haplotype graph to generate a final haplotype-resolved assembly graph; and
reconstructing haplotype-specific contigs from the final haplotype-resolved assembly graph resulting in haplotype-specific contigs of at least 120 megabase pairs of the diploid genome for the diploid genomic sample;
wherein generating the plurality of haplotype-specific assembly graphs using phased reads and haplotype aware overlapping of the phased reads further comprises:
for each respective haplotype-fused contig in the plurality of haplotype-fused configs, identifying a subset of raw sequence reads in the plurality of sequence reads that belong to that the respective haplotype-fused contig;
phasing the sequence reads to sort the sequence reads into groups representing different haplotypes using single nucleotide polymorphism (SNP) information; and
phasing the sequence reads from the same contig by block and phase.

* * * * *